United States Patent
Yeung

(10) Patent No.: US 9,182,383 B2
(45) Date of Patent: Nov. 10, 2015

(54) BIOMARKERS FOR THE DIAGNOSIS AND TREATMENT OF PANCREATIC CANCER

(71) Applicant: The Institute for Cancer Research, Philadelphia, PA (US)

(72) Inventor: Anthony T. Yeung, Huntingdon Valley, PA (US)

(73) Assignee: The Institute for Cancer Research, Philadelphia, PA (US)

( * ) Notice: Subject to any disclaimer, the term of this patent is extended or adjusted under 35 U.S.C. 154(b) by 0 days.

(21) Appl. No.: 14/109,241

(22) Filed: Dec. 17, 2013

(65) Prior Publication Data

US 2014/0103204 A1  Apr. 17, 2014

Related U.S. Application Data

(60) Division of application No. 12/812,394, filed on Aug. 18, 2010, now Pat. No. 8,609,437, which is a continuation-in-part of application No. PCT/US2009/031587, filed on Jan. 21, 2009.

(60) Provisional application No. 61/021,772, filed on Jan. 17, 2008.

(51) Int. Cl.
*G01N 33/487* (2006.01)
*G01N 33/48* (2006.01)
*C12Q 1/68* (2006.01)
*G01N 33/00* (2006.01)

(52) U.S. Cl.
CPC ............ *G01N 33/487* (2013.01); *C12Q 1/6886* (2013.01); *C12Q 1/68* (2013.01); *C12Q 2600/158* (2013.01); *G01N 33/00* (2013.01); *G01N 33/48* (2013.01)

(58) Field of Classification Search
CPC ... G01N 33/487; G01N 33/483; G01N 33/48; G01N 33/00; C12Q 1/6886; C12Q 1/6883; C12Q 1/6876; C12Q 1/68; C12Q 1/00
USPC .......................................................... 436/518
See application file for complete search history.

(56) References Cited

U.S. PATENT DOCUMENTS

| | | | |
|---|---|---|---|
| 2002/0034773 A1 * | 3/2002 | Hanash et al. | 435/7.23 |
| 2002/0150894 A1 | 10/2002 | Batra et al. | |
| 2005/0009067 A1 | 1/2005 | Logsdon et al. | |
| 2006/0228300 A1 * | 10/2006 | Chang et al. | 424/1.49 |
| 2007/0140966 A1 | 6/2007 | Chang et al. | |
| 2007/0231822 A1 | 10/2007 | Mitas et al. | |
| 2007/0243547 A1 * | 10/2007 | Cheng et al. | 435/6 |

OTHER PUBLICATIONS

Wang, Y., et al. "Diagnostic value of mucins (MUC1, MUC2 and MUC5AC) expression profile in endoscopic ultrasound-guided fine-needle aspiration specimens of the pancreas." Int J Cancer. Dec. 15, 2007;121(12):2716-22.
Gesierich, S., et al. "Colocalization of the tetraspanins, CO-029 and CD151, with integrins in human pancreatic adenocarcinoma: impact on cell motility." Clin Cancer Res. Apr. 15, 2005;11(8):2840-52.

* cited by examiner

*Primary Examiner* — Christine T Mui
(74) *Attorney, Agent, or Firm* — Kathleen D. Rigaut; Dann, Dorfman, Herrell and Skillman, P.C.

(57) ABSTRACT

Compositions and methods for use in methods and kits for the detection of an increased risk of pancreatic cancer are provided. Cyst fluid samples isolated from patients that are positive for at least three of the following markers, mucin 1, mucin 2, mucin 5AC, mucin 5B, mucin 6, CEA CAM 1, CEACAM 5, CEACAM 6, CEACAM 7, CEACAM 8, S100-A6, S100-A8, S100-A9 and S100-A11 indicate that such patients are at greater risk for development of pancreatic cancer when compared to cyst fluid samples isolated from patients lacking these markers.

9 Claims, 18 Drawing Sheets

Figure 1

| Cyst # | 15 | 6 | 8 | 10 | 1 | 2 | 4 | 16 | 18 | 13 | 7 |
|---|---|---|---|---|---|---|---|---|---|---|---|
| Histology | - | - | - | - | - | - | - | - | - | - | - |
| CEA | - | - | - | - | <0.1 | 1.8 | 49.4 | 60.5 | 176 | 182 | 231 |
| Amylase | - | - | - | - | - | 56 | - | - | - | 163400 | 12330 |
| Cytology | A | A | A | C | A | A | C | A | A | A | A |
| Gender | F | F | F | M | F | F | F | F | F | M | M |
| Age | 33 | 53 | 83 | 50 | 51 | 74 | 73 | 56 | 76 | 67 | 63 |
| Cyst size | 15 mm x 12 mm | 14 mm x 17 mm | 22 mm x 14 mm | 18 mm x 28 mm | 16 mm x 13 mm | 20 mm x 24 mm | 31 mm x 11 mm | 34 mm x 32 mm | 22 mm x 14 mm | 24 mm x 17 mm | 23 mm x 10 mm |
| Location | pancreatic tail | pancreatic tail | pancreatic head | pancreatic body | pancreatic body | pancreatic tail | pancreatic neck | pancreatic body | pancreatic head | pancreatic head | pancreatic body |

| Cyst # | 11 | 17 | 14 | 9 | 19A | 19B | 12 | 5 | 3 | 21 |
|---|---|---|---|---|---|---|---|---|---|---|
| Histology | - | IPMN adenoma | MCA | - | - | IPMN adenoma | - | Adeno-carcinoma | - | MCA |
| CEA | 333 | 410 | 582 | 797 | 2853 | - | 5115 | 14175 | 63,830 | - |
| Amylase | 43152 | 25600 | 4036 | 75210 | - | - | - | 6 | - | - |
| Cytology | A | A | A | A | A | A | A | C | A | A |
| Gender | F | M | F | M | M | M | F | M | F | F |
| Age | 81 | 77 | 45 | 68 | 81 | 81 | 65 | 70 | 73 | 32 |
| Cyst size | 27 mm x 10 mm | 23 mm x 26 mm | 46 mm x 47 mm | 29 mm x 21 mm | 22 mm x 20 mm | - | 14 mm x 9 mm | 18 mm x 18 mm | 17 mm x 13 mm | - |
| Location | pancreatic tail | uncinate portion of pancreatic head | - | pancreatic head | pancreatic tail | - | pancreatic head | pancreatic body/tail | pancreatic head | - |

Table I. Clinical information for the pancreatic cyst fluid samples. CEA (ng/mL) and Amylase (units/mL) are results from clinical lab immuno assays. MCA=mucinous cystadenoma. Cytology categories: A- Benign: No evidence of benign mucinous epithelium, atypical cells or carcinoma. C- Atypical/suspicious cytology.

| Cyst # | 15 | 6 | 8 | 10 | 1 | 2 | 4 | 16 | 18 | 13 | 7 | 11 | 17 | 14 | 9 | 19A | 19B | 12 | 5 | 3 | 21 |
|---|---|---|---|---|---|---|---|---|---|---|---|---|---|---|---|---|---|---|---|---|---|
| Histology | | | | | | | | | | | | | IPMN adenoma | MCA | | | IPMN adenoma | | Adeno-carcinoma | | MCA |
| CEA | - | - | - | - | <0.1 | 2 | 49 | 61 | 176 | 182 | 231 | 333 | 410 | 582 | 797 | 2853 | - | 5115 | 14175 | 63830 | - |
| Serum albumin | 10.4 | 9.3 | 7.0 | 5.5 | 6.6 | 5.5 | | 1.8 | | 2.4 | | 0.8 | 1.4 | 7.4 | 0.1 | 1.1 | 7.0 | 0.4 | 7.9 | 7.0 | 9.9 |
| Alpha-1-antitrypsin | 4.9 | 4.0 | 0.6 | 1.7 | 1.5 | 2.7 | 0.5 | 2.2 | 0.5 | 2.2 | 0.2 | 0.5 | 0.4 | 3.6 | 0.3 | | 0.2 | 1.3 | 4.4 | 1.3 | 1.7 |
| Serotransferrin | 7.2 | 5.8 | 2.4 | 3.1 | 4.9 | 3.7 | | 4.2 | | 1.0 | | 0.7 | | 6.8 | | 0.1 | 3.3 | 0.1 | 5.8 | 3.7 | 5.5 |
| Apolipoprotein A-I | 7.1 | 4.7 | 4.7 | 10.4 | 0.8 | 4.7 | | | | | | | 0.3 | 0.6 | | | 0.3 | | 11.8 | 4.7 | 1.3 |
| Transthyretin | 1.4 | 1.4 | 0.2 | 0.2 | 0.2 | 1.4 | | 1.4 | | | | | | 0.6 | | | | | 1.4 | 0.6 | 0.2 |
| Apolipoprotein A-II | 0.8 | | | | 0.4 | 0.8 | | | | | | | | | | | | | 2.3 | | 0.4 |
| Alpha-1-acid glycoprotein 1 | 1.4 | 1.8 | 0.8 | 1.4 | 0.6 | 1.4 | | 0.8 | | 0.8 | | 0.6 | 0.2 | 1.4 | | | 0.4 | 0.2 | 2.3 | 0.8 | 0.6 |
| Alpha-1-acid glycoprotein 2 | 1.1 | 1.1 | 0.6 | 0.8 | | 1.4 | | 0.4 | | | | | | 1.1 | | | 0.2 | | 1.4 | | 0.4 |
| Zinc-alpha-2-glycoprotein | 0.7 | 1.1 | 0.2 | 1.3 | 0.1 | 1.1 | | 0.9 | | 0.7 | | 0.1 | | 0.7 | | 0.1 | 0.4 | 0.1 | 1.3 | 0.2 | 0.2 |
| Alpha-2-macroglobulin | 0.3 | 0.1 | 0.6 | 0.5 | | 0.9 | | 0.3 | | | | | | 0.1 | | | 0.4 | | 0.4 | 0.1 | 0.7 |
| Vitamin D-binding protein | 2.1 | 1.5 | 0.7 | 0.5 | 1.4 | 0.4 | | 0.1 | | 0.0 | | | | 0.3 | | | 0.4 | | 1.4 | 0.1 | 0.9 |
| Complement C3 | 0.4 | 0.6 | 0.4 | 0.7 | 0.1 | 0.9 | | 0.6 | | | | | | 0.5 | | | 0.4 | 0.1 | 1.2 | 0.3 | 0.6 |
| Hemoglobin subunit alpha | | 0.3 | 2.1 | 1.0 | | 1.0 | | 0.2 | | 0.2 | | | | | | | | | 2.1 | | 1.0 |
| Hemoglobin subunit beta | | 1.4 | 19.7 | 3.6 | | 6.0 | | | | | | | | | | | | | 19.7 | | 1.4 |
| Haptoglobin alpha beta chain | 1.4 | | 2.0 | 1.4 | | 0.2 | | | | | | | | | | | 0.7 | | 2.5 | 0.7 | |
| Ig gamma-1 chain C region | 2.6 | 2.2 | 1.7 | 1.7 | 1.7 | 1.4 | | 1.4 | | 1.2 | | 1.2 | 0.1 | 1.9 | | | 1.4 | | 2.6 | 1.9 | 2.6 |
| Ig gamma-2 chain C region | 1.9 | 1.9 | 1.2 | 1.7 | 1.2 | 1.2 | | 1.7 | | 0.2 | | 0.5 | 0.1 | 1.4 | | | 1.2 | 0.1 | 1.7 | 1.7 | 1.9 |

Table 2. Representatives of 137 plasma proteins distributed among the pancreatic cyst samples. The numbers shown are emPAI scores which are roughly proportional to protein abundance. Dark (>1), medium (0.1 to 1), and light (<0.1) shading denotes relative protein abundance. No proteins were detected for the empty boxes. CEA = ng/mL.

Figure 2A

| | Mass | SwissProt name | Title | Cyst 18 | Cyst 7 | Cyst 4 | Cyst 13 | Cyst 16 | Cyst 11 | Cyst 9 | Cyst 12 | Cyst 17 | Cyst 3 | Cyst 14 | Cyst 19 | Cyst 20 |
|---|---|---|---|---|---|---|---|---|---|---|---|---|---|---|---|---|
| 1 | 71317 | ALBU_HUMAN | Serum albumin | - | 0.05 | 0.05 | 3.83 | 2.38 | 1.04 | - | 0.11 | 0.58 | 17.1 | 16.2 | 1.49 | 15.3 |
| 2 | 30759 | APOA1_HUMAN | Apolipoprotein A-I | - | - | - | - | - | - | - | - | - | 4.69 | 0.42 | - | - |
| 3 | 16102 | HBB_HUMAN | Hemoglobin subunit beta | - | - | - | - | 0.24 | - | - | - | - | - | - | - | - |
| 4 | 79280 | TRFE_HUMAN | Serotransferrin | - | - | - | 1.38 | 3.32 | 0.58 | - | 0.05 | - | 8.83 | 11.4 | - | 2.94 |
| 5 | 46878 | A1AT_HUMAN | Alpha-1-antitrypsin | 0.47 | 0.08 | 0.36 | 5.31 | 2.98 | 0.59 | 0.26 | 1.51 | 0.26 | 1.33 | 4.42 | - | 0.17 |
| 6 | 15991 | TTHY_HUMAN | Transthyretin | - | - | - | - | 1.39 | - | - | - | - | 0.24 | 0.92 | - | - |
| 7 | 11773 | KAC_HUMAN | Ig kappa chain C region | - | - | - | 0.79 | 3.28 | - | - | - | - | 3.28 | 4.73 | - | 2.2 |
| 8 | 11282 | APOA2_HUMAN | Apolipoprotein A-II | - | - | - | - | - | - | - | - | - | - | 0.35 | - | - |
| 9 | 11401 | LAC_HUMAN | Ig lambda chain C regions | - | - | - | 2.3 | 3.45 | 1.45 | - | 0.35 | 0.35 | 2.3 | 5 | - | 2.3 |
| 10 | 23725 | A1AG1_HUMAN | Alpha-1-acid glycoprotein 1 | - | - | - | 1.44 | 1.11 | 0.56 | - | 0.16 | - | 0.35 | 1.84 | - | 0.35 |
| 11 | 23873 | A1AG2_HUMAN | Alpha-1-acid glycoprotein 2 | - | - | - | 1.1 | 0.56 | - | - | - | - | - | 1.43 | - | - |
| 12 | 36596 | IGHG1_HUMAN | Ig gamma-1 chain C region | - | - | - | 1.41 | 1.66 | 1.19 | - | 0.1 | - | 1.93 | 2.23 | - | 1.41 |
| 13 | 36489 | IGHG2_HUMAN | Ig gamma-2 chain C region | - | - | - | 0.22 | 1.94 | 0.48 | - | - | - | 1.66 | 2.24 | - | 2.24 |
| 14 | 33222 | IGHG3_HUMAN | Ig gamma-3 chain C region | - | - | - | 0.38 | - | - | - | - | - | 0.71 | 1.12 | - | 1.93 |
| 15 | 34079 | ZA2G_HUMAN | Zinc-alpha-2-glycoprotein | - | - | - | 0.69 | 0.37 | 0.11 | - | 0.11 | - | 0.23 | 0.37 | - | 0.37 |
| 16 | 15305 | HBA_HUMAN | Hemoglobin subunit alpha | - | - | - | - | 0.57 | - | - | - | - | - | - | - | - |
| 17 | 55347 | IC1_HUMAN | Plasma protease C1 inhibitor | - | - | - | 0.07 | 0.07 | - | - | 0.3 | - | 0.3 | 0.58 | - | 0.07 |
| 18 | 164600 | A2MG_HUMAN | Alpha-2-macroglobulin | - | - | - | - | 0.14 | - | - | - | - | 0.02 | 0.09 | - | 0.3 |
| 19 | 11882 | KV302_HUMAN | Ig kappa chain V-III region SIE | - | - | - | - | - | - | - | - | - | 1.37 | 0.78 | - | 0.33 |
| 20 | 122983 | CERU_HUMAN | Ceruloplasmin | - | - | - | - | - | - | - | - | - | 0.03 | - | - | 0.03 |
| 21 | 12422 | KV204_HUMAN | Ig kappa chain V-II region TEW | - | - | - | - | - | - | - | - | - | 0.74 | - | - | - |
| 22 | 188569 | CO3_HUMAN | Complement C3 | - | - | - | 0.02 | 0.04 | - | - | 0.06 | - | 0.04 | 0.29 | - | 0.24 |
| 23 | 40098 | FETUA_HUMAN | Alpha-2-HS-glycoprotein | - | - | - | 0.09 | - | - | - | - | - | - | - | - | - |

Figure 2B

| | | | | | | | | | | | | | | | |
|---|---|---|---|---|---|---|---|---|---|---|---|---|---|---|---|
| 24 | 54526 | VTDB_HUMAN | Vitamin D-binding protein | - | - | - | - | - | - | - | - | - | 0.14 | 0.22 | - | 0.07 |
| 25 | 54809 | A1BG_HUMAN | Alpha-1B-glycoprotein | - | - | - | - | - | - | - | - | - | 0.39 | 0.22 | - | - |
| 26 | 20064 | FRIL_HUMAN | Ferritin light chain | - | - | 1.01 | - | - | - | - | - | - | 0.42 | 0.42 | - | - |
| 27 | 266034 | FINC_HUMAN | Fibronectin | - | - | - | - | - | - | - | - | - | 0.57 | - | - | 0.03 |
| 28 | 11895 | KV106_HUMAN | Ig kappa chain V-I region EU | - | - | - | - | - | - | - | - | - | - | - | - | - |
| 29 | 12099 | KV101_HUMAN | Ig kappa chain V-I region AG | - | - | - | - | - | - | - | - | - | 0.33 | - | - | 0.33 |
| 30 | 12042 | LV302_HUMAN | Ig lambda chain V-III region LOI | - | - | - | - | - | - | - | - | - | 0.33 | - | - | 0.33 |
| 31 | 52385 | HEMO_HUMAN | Hemopexin | - | 0.07 | - | - | - | - | - | - | - | 0.41 | 0.62 | - | 0.32 |
| 32 | 39886 | AMBP_HUMAN | AMBP protein [Contains: Alpha-1-microglobulin] | - | - | - | - | - | - | - | - | - | 0.2 | - | - | - |
| 33 | 12681 | KV309_HUMAN | Ig kappa chain V-III region VG | - | - | - | - | - | - | - | - | - | 0.31 | - | - | 0.31 |
| 34 | 45861 | HPT_HUMAN | Haptoglobin [Contains: Haptoglobin alpha chain; Haptoglobin beta chain] | - | 0.27 | - | - | - | - | - | - | - | 1.19 | 0.37 | - | 1.77 |
| 35 | 47792 | AACT_HUMAN | Alpha-1-antichymotrypsin | - | 0.25 | 0.83 | - | - | - | - | 0.46 | - | 0.08 | 0.46 | 0.16 | 0.16 |
| 36 | 52106 | FIBG_HUMAN | Fibrinogen gamma chain | - | - | - | - | - | - | - | - | - | - | 0.07 | - | 0.15 |
| 37 | 95656 | FIBA_HUMAN | Fibrinogen alpha chain [Contains: Fibrinopeptide A] | - | - | - | - | - | - | - | - | - | - | - | - | 0.08 |
| 38 | 38486 | IGHA1_HUMAN | Ig alpha-1 chain C region | - | - | 0.2 | 0.45 | - | - | - | 0.45 | 0.59 | 0.92 | 0.92 | 0.45 | 0.45 |
| 39 | 21383 | FRIH_HUMAN | Ferritin heavy chain | - | - | 0.39 | - | - | - | - | - | - | - | 0.39 | - | - |
| 40 | 56577 | FIBB_HUMAN | Fibrinogen beta chain [Contains: Fibrinopeptide B] | - | - | - | - | 0.14 | - | - | - | - | - | - | - | 0.47 |
| 41 | 60510 | HRG_HUMAN | Histidine-rich glycoprotein | - | - | - | - | - | - | - | - | - | - | - | - | - |
| 42 | 28909 | CAH1_HUMAN | Carbonic anhydrase 1 | - | - | - | - | - | - | - | - | - | - | - | - | - |
| 43 | 42052 | ACTB_HUMAN | Actin, cytoplasmic 1 | 0.19 | - | - | - | - | - | - | - | - | - | - | - | 0.53 |
| 44 | 143654 | CFAH_HUMAN | Complement factor H | - | - | - | - | - | - | - | - | - | - | 0.05 | - | 0.22 |
| 45 | 103489 | ITIH4_HUMAN | Inter-alpha-trypsin inhibitor heavy chain H4 | - | - | - | - | - | - | - | - | - | 0.04 | - | - | - |

Figure 2C

| # | ID | Code | Name | | | | | | | | | | | |
|---|---|---|---|---|---|---|---|---|---|---|---|---|---|---|
| 46 | 194247 | CO4A_HUMAN | Complement C4-A | - | - | - | - | - | - | - | - | - | - | - |
| 47 | 53031 | CLUS_HUMAN | Clusterin | - | - | - | - | - | - | - | - | - | - | 0.5 |
| 48 | 40022 | IDH3A_HUMAN | Isocitrate dehydrogenase [NAD] subunit alpha, mitochondrial | - | - | 0.09 | 0.09 | - | - | - | - | - | - | - |
| 49 | 23337 | RETBP_HUMAN | Plasma retinol-binding protein | - | - | - | 0.35 | - | - | - | 0.16 | - | - | - |
| 50 | 46484 | PEDF_HUMAN | Pigment epithelium-derived factor | - | - | - | - | - | - | - | - | - | - | 0.08 |
| 51 | 13671 | HV310_HUMAN | Ig heavy chain V-III region HIL | - | - | - | - | - | - | - | - | - | - | 0.29 |
| 52 | 12836 | HV320_HUMAN | Ig heavy chain V-III region GAL | - | - | - | - | - | - | - | - | - | - | - |
| 53 | 38747 | LUM_HUMAN | Lumican | - | - | - | - | - | - | - | - | - | - | - |
| 54 | 12462 | HV304_HUMAN | Ig heavy chain V-III region TIL | - | - | - | 0.32 | - | - | - | - | 0.32 | - | - |
| 55 | 12003 | LV102_HUMAN | Ig lambda chain V-I region HA | - | - | - | - | - | - | - | - | 0.33 | - | - |
| 56 | 39584 | APOH_HUMAN | Beta-2-glycoprotein 1 | - | - | - | - | - | - | - | - | - | - | - |
| 57 | 36431 | IGHG4_HUMAN | Ig gamma-4 chain C region | - | - | - | 0.99 | - | - | - | 0.8 | 0.99 | - | - |
| 58 | 53025 | ANT3_HUMAN | Antithrombin-III | - | - | - | 1.59 | - | - | - | - | 0.5 | - | - |
| 59 | 12746 | KV402_HUMAN | Ig kappa chain V-IV region Len | - | - | - | 0.71 | - | - | - | 0.71 | 0.31 | - | - |
| 60 | 66202 | LG3BP_HUMAN | Galectin-3-binding protein | - | - | - | - | - | 0.06 | - | 0.73 | 0.06 | - | 0.82 |
| 61 | 123407 | SDCG1_HUMAN | Serologically defined colon cancer antigen 1 | - | - | - | - | - | - | - | - | - | - | - |
| 62 | 13332 | HV305_HUMAN | Ig heavy chain V-III region BRO | - | - | - | - | - | - | - | - | - | - | - |
| 63 | 11768 | KV105_HUMAN | Ig kappa chain V-I region DEE | - | - | - | - | - | - | - | - | - | - | - |
| 64 | 55069 | VTNC_HUMAN | Vitronectin | - | - | - | - | - | - | - | 0.07 | - | - | - |
| 65 | 50210 | MUC_HUMAN | Ig mu chain C region | - | - | - | - | - | - | - | 0.07 | 1.37 | - | 0.07 |
| 66 | 70963 | AFAM_HUMAN | Afamin | - | - | - | - | - | - | - | 0.11 | - | - | - |

Figure 2D

| # | ID | Name | Description | V1 | V2 | V3 | V4 | V5 | V6 | V7 | V8 | V9 |
|---|---|---|---|---|---|---|---|---|---|---|---|---|
| 67 | 23840 | TIMP1_HUMAN | Metalloproteinase inhibitor 1 | - | - | - | - | 0.35 | 0.35 | 1.82 | 0.35 | 0.16 |
| 68 | 165215 | PZP_HUMAN | Pregnancy zone protein | - | - | 0.02 | 0.05 | - | - | - | - | 0.07 |
| 69 | 72996 | KNG1_HUMAN | Kininogen-1 | - | - | - | - | - | - | - | - | - |
| 70 | 54873 | A2AP_HUMAN | Alpha-2-antiplasmin | - | - | 0.14 | 0.39 | - | - | - | 0.07 | - |
| 71 | 101782 | ITIH1_HUMAN | Inter-alpha-trypsin inhibitor heavy chain H1 | - | - | - | - | - | - | - | - | - |
| 72 | 16187 | HBG1_HUMAN | Hemoglobin subunit gamma-1 | - | - | - | 0.24 | - | - | - | - | - |
| 73 | 516666 | APOB_HUMAN | Apolipoprotein B-100 | - | - | - | 0.01 | - | - | - | - | - |
| 74 | 189923 | CO5_HUMAN | Complement C5 [Contains: Complement C5 beta chain; Complement C5 alpha chain; C5a anaphylatoxin; Complement C5 alpha~ chain] | - | - | - | - | - | - | - | - | 0.03 |
| 75 | 108367 | CO6_HUMAN | Complement component C6 | - | - | - | - | - | - | - | - | - |
| 76 | 13114 | HV103_HUMAN | Ig heavy chain V-I region V35 | - | - | - | - | - | - | - | - | - |
| 77 | 11500 | LV301_HUMAN | Ig lambda chain V-III region SH | - | - | - | - | - | - | - | - | - |
| 78 | 12863 | KV310_HUMAN | Ig kappa chain V-III region VH | - | - | - | - | - | - | 0.31 | 0.31 | - |
| 79 | 80014 | TRFL_HUMAN | Lactotransferrin | - | - | - | 0.5 | - | - | - | 0.65 | - |
| 80 | 42829 | ILEU_HUMAN | Leukocyte elastase inhibitor | 0.48 | - | - | - | - | - | - | - | - |
| 81 | 8560 | UBIQ_HUMAN | Ubiquitin | - | - | - | 1.18 | 1.18 | - | - | - | 0.48 |
| 82 | 15123 | LEG7_HUMAN | Galectin-7 | 0.17 | - | - | 0.58 | - | - | - | - | - |
| 83 | 45037 | CATD_HUMAN | Cathepsin D | - | - | - | 0.17 | - | - | - | - | - |
| 84 | 27947 | CASPE_HUMAN | Caspase-14 | 0.46 | - | - | 0.14 | - | - | - | - | - |
| 85 | 59947 | CATA_HUMAN | Catalase | - | - | - | 0.13 | - | - | - | - | - |

Figure 2E

| | | | | | | | | | | |
|---|---|---|---|---|---|---|---|---|---|---|
| 86 | 37139 | APRV1_HUMAN | Retroviral-like aspartic protease 1 | - | - | - | - | - | - | - |
| 87 | 76926 | TGM3_HUMAN | Protein-glutamine gamma-glutamyltransferase E | - | - | 0.1 | - | - | - | - |
| 88 | 334021 | DESP_HUMAN | Desmoplakin | 0.04 | - | 0.1 | - | - | - | - |
| 89 | 105392 | OCRL_HUMAN | Inositol polyphosphate 5-phosphatase OCRL-1 | - | 0.04 | 0.06 | 0.04 | - | - | - |
| 90 | 82376 | PLAK_HUMAN | Junction plakoglobin | 0.14 | - | 0.04 | - | - | - | - |
| 91 | 112640 | NFH_HUMAN | Neurofilament heavy polypeptide | 0.03 | - | 0.03 | 0.03 | - | 0.03 | - |
| 92 | 115417 | PA24B_HUMAN | Cytosolic phospholipase A2 beta | - | - | 0.03 | 0 | - | - | - |
| 93 | 129242 | RPC2_HUMAN | DNA-directed RNA polymerase III subunit RPC2 | - | - | 0.03 | 0.03 | - | - | - |
| 94 | 199928 | RGPD5_HUMAN | RANBP2-like and GRIP domain-containing protein 5 | - | - | 0.02 | - | - | - | - |
| 95 | 43543 | MUCB_HUMAN | Ig mu heavy chain disease protein | - | - | - | - | - | - | - |
| 96 | 102013 | B3AT_HUMAN | Band 3 anion transport protein | - | - | - | - | - | 0.09 | 0.78 |
| 97 | 16389 | HV209_HUMAN | Ig heavy chain V-II region ARH-77 | - | - | - | - | - | - | - |
| 98 | 15684 | HBAZ_HUMAN | Hemoglobin subunit zeta | - | - | - | - | - | - | - |
| 99 | 13486 | KV401_HUMAN | Ig kappa chain V-IV region | - | - | - | - | - | - | - |
| 100 | 16159 | HBD_HUMAN | Hemoglobin subunit delta | - | - | - | - | - | - | - |
| 101 | 16249 | HBE_HUMAN | Hemoglobin subunit epsilon | - | - | - | - | - | - | - |
| 102 | 11810 | KV104_HUMAN | Ig kappa chain V-I region CAR | - | - | - | - | - | - | - |
| 103 | 12931 | KV110_HUMAN | Ig kappa chain V-I region HK102 | - | - | - | - | - | - | - |

Figure 2F

| | | | | | | | | | | | | |
|---|---|---|---|---|---|---|---|---|---|---|---|---|
| 104 | 53406 | ANGT_HUMAN | Angiotensinogen | - | - | - | - | - | - | - | 0.07 | - |
| 105 | 38777 | FHR1_HUMAN | Complement factor H-related protein 1 | - | - | - | - | - | - | - | - | - |
| 106 | 84583 | CO2_HUMAN | Complement C2 | - | - | - | - | - | - | - | - | - |
| 107 | 45371 | APOA4_HUMAN | Apolipoprotein A-IV | - | - | - | - | - | - | - | - | - |
| 108 | 11889 | KV116_HUMAN | Ig kappa chain V-I region Roy | - | - | - | - | - | - | - | - | - |
| 109 | 12745 | HV303_HUMAN | Ig heavy chain V-III region VH26 | - | - | - | - | - | - | - | - | - |
| 110 | 11192 | PLGB_HUMAN | Plasminogen-related protein B | - | - | - | - | - | - | - | - | - |
| 111 | 11715 | KV119_HUMAN | Ig kappa chain V-I region Wes | - | - | - | - | - | - | - | - | - |
| 112 | 11941 | KV113_HUMAN | Ig kappa chain V-I region Lay | - | - | - | 0.33 | - | - | - | - | 0.33 |
| 113 | 86847 | CFAB_HUMAN | Complement factor B | - | - | - | - | - | - | - | - | - |
| 114 | 68072 | CFAI_HUMAN | Complement factor I | - | - | - | - | - | - | - | - | 0.11 |
| 115 | 36246 | APOE_HUMAN | Apolipoprotein E | - | - | - | - | - | - | - | - | - |
| 116 | 39895 | PON1_HUMAN | Serum paraoxonase/arylesterase 1 | - | - | - | - | - | - | - | - | - |
| 117 | 11624 | LV403_HUMAN | Ig lambda chain V-IV region Hil | - | - | - | - | - | - | - | - | - |
| 118 | 21547 | APOD_HUMAN | Apolipoprotein D | - | - | - | - | - | - | - | - | - |
| 119 | 86043 | GELS_HUMAN | Gelsolin | - | - | - | - | - | - | 0.04 | - | 0.52 |
| 120 | 96650 | CO7_HUMAN | Complement component C7 | - | - | - | - | - | - | 0.04 | - | - |
| 121 | 12782 | KV201_HUMAN | Ig kappa chain V-II region Cum | - | - | - | 0.31 | - | - | 0.31 | - | 0.31 |
| 122 | 93247 | PLMN_HUMAN | Plasminogen | - | - | - | - | - | - | 0.04 | - | - |
| 123 | 16041 | IGJ_HUMAN | Immunoglobulin J chain | - | - | - | - | - | - | 1.38 | - | - |
| 124 | 11752 | CO005_HUMAN | Uncharacterized protein C15orf5 | - | - | - | - | - | - | 0.34 | - | - |

Figure 2G

| # | ID | Name | | | | | | | | | | | | |
|---|---|---|---|---|---|---|---|---|---|---|---|---|---|---|
| 125 | 13059 | HV313_HUMAN | Ig heavy chain V-III region POM | - | - | - | - | - | - | - | - | - | - | - |
| 126 | 34454 | FCN2_HUMAN | Ficolin-2 | - | - | - | - | - | - | - | - | 0.3 | 0.11 | - | - |
| 127 | 40624 | RAI3_HUMAN | Retinoic acid-induced protein 3 | - | - | - | - | - | - | - | - | - | 0.09 | - | - |
| 128 | 61187 | CH60_HUMAN | 60 kDa heat shock protein, mitochondrial | - | - | - | - | - | - | - | - | - | 0.06 | - | - |
| 129 | 58259 | MMSA_HUMAN | Methylmalonate-semialdehyde dehydrogenase [acylating], mitochondrial | - | - | 0.06 | - | - | - | - | - | - | 0.06 | - | - |
| 130 | 69484 | EZRI_HUMAN | Ezrin | - | - | - | - | - | - | 0.11 | - | - | 0.05 | - | 0.05 |
| 131 | 596494 | FCGBP_HUMAN | IgGFc-binding protein | - | - | - | - | - | - | - | 0.01 | - | 0.02 | - | - |
| 132 | 168870 | MRC1_HUMAN | Macrophage mannose receptor 1 | - | - | - | - | - | - | - | - | - | 0.02 | - | - |
| 133 | 514737 | APOA_HUMAN | Apolipoprotein(a) | - | - | - | - | - | - | - | - | - | - | - | - |
| 134 | 59703 | K1C10_HUMAN | Keratin, type I cytoskeletal 10 | 3.82 | 1.79 | 1.48 | - | 5.92 | 1.63 | 0.72 | 1.33 | 3.02 | 0.35 | 0.94 | 0.35 |
| 135 | 51875 | K1C14_HUMAN | Keratin, type I cytoskeletal 14 | 0.52 | 0.52 | 0.63 | - | 0.74 | 0.87 | 0.23 | 0.32 | 0.52 | 0.23 | 0.15 | 0.15 |
| 136 | 44065 | K1C19_HUMAN | Keratin, type I cytoskeletal 19 | 0.18 | - | 0.28 | 0.08 | 0.28 | - | 0.28 | - | - | 0.18 | - | 0.18 |
| 137 | 53671 | K2C8_HUMAN | Keratin, type II cytoskeletal 8 | 0.22 | 0.07 | - | - | 0.14 | 0.31 | - | 0.07 | 0.22 | - | 0 | - |

Figure 2H

| | Mass | SwissProt name | Title | Cyst 5 | Cyst 21 | Cyst 8 | Cyst 15 | Cyst 6 | Cyst 1 | Cyst 10 | Cyst 2 |
|---|---|---|---|---|---|---|---|---|---|---|---|
| 1 | 71317 | ALBU_HUMAN | Serum albumin | 18 | 14.5 | 19 | 18 | 16.2 | 18 | 13 | 16.2 |
| 2 | 30759 | APOA1_HUMAN | Apolipoprotein A-I | 21.9 | 0.79 | 3.51 | 8.05 | 4.69 | 0.42 | 21.9 | 11.8 |
| 3 | 16102 | HBB_HUMAN | Hemoglobin subunit beta | 12.4 | 1.38 | 15.7 | - | - | - | 2.66 | 9.81 |
| 4 | 79280 | TRFE_HUMAN | Serotransferrin | 4.68 | 3.95 | 3.12 | 5.82 | 6.47 | 7.19 | 3.95 | 6.82 |
| 5 | 46878 | A1AT_HUMAN | Alpha-1-antitrypsin | 4.85 | 2.16 | 0.59 | 2.98 | 4.02 | 1.71 | 2.16 | 5.31 |
| 6 | 15991 | TTHY_HUMAN | Transthyretin | 3.59 | 0.24 | 0.24 | 2.69 | 2.69 | 0.24 | 0.24 | 3.59 |
| 7 | 11773 | KAC_HUMAN | Ig kappa chain C region | 3.28 | 1.39 | 4.73 | 4.73 | 6.66 | 2.2 | 4.73 | 3.28 |
| 8 | 11282 | APOA2_HUMAN | Apolipoprotein A-II | 10.2 | 0.35 | - | 0.83 | - | - | - | 2.34 |
| 9 | 11401 | LAC_HUMAN | Ig lambda chain C regions | 5 | 2.3 | 3.45 | 3.45 | 2.3 | 3.45 | 2.3 | 2.3 |
| 10 | 23725 | A1AG1_HUMAN | Alpha-1-acid glycoprotein 1 | 2.29 | 0.81 | 0.81 | 1.11 | 2.29 | 0.56 | 1.11 | 1.84 |
| 11 | 23873 | A1AG2_HUMAN | Alpha-1-acid glycoprotein 2 | 2.8 | - | 0.35 | 0.56 | 1.82 | - | 1.82 | 1.82 |
| 12 | 36596 | IGHG1_HUMAN | Ig gamma-1 chain C region | 2.56 | 1.66 | 1.66 | 1.66 | 1.66 | 1.66 | 2.23 | 1.66 |
| 13 | 36489 | IGHG2_HUMAN | Ig gamma-2 chain C region | 1.66 | 1.94 | 1.94 | 2.24 | 2.24 | 1.42 | 2.58 | 1.66 |
| 14 | 33222 | IGHG3_HUMAN | Ig gamma-3 chain C region | 1.12 | 1.93 | 1.37 | 1.12 | 1.63 | 0.71 | 1.12 | 1.63 |
| 15 | 34079 | ZA2G_HUMAN | Zinc-alpha-2-glycoprotein | 1.57 | 0.11 | 0.11 | 0.37 | 1.08 | 0.11 | 1.08 | 1.57 |
| 16 | 15305 | HBA_HUMAN | Hemoglobin subunit alpha | 2.9 | 1.48 | 2.9 | - | 0.25 | - | 1.48 | 0.97 |
| 17 | 55347 | IC1_HUMAN | Plasma protease C1 inhibitor | 0.92 | 0.3 | 0.22 | 0.38 | 0.38 | 0.07 | 0.8 | 0.92 |
| 18 | 164600 | A2MG_HUMAN | Alpha-2-macroglobulin | 0.39 | 0.49 | 0.78 | 0.17 | 0.05 | - | 0.42 | 0.82 |
| 19 | 11882 | KV302_HUMAN | Ig kappa chain V-III region SIE | 1.37 | 0.78 | - | 0.78 | 0.78 | - | 0.78 | 0.78 |
| 20 | 122983 | CERU_HUMAN | Ceruloplasmin | 0.56 | 0.34 | 0.09 | 0.47 | 0.13 | 0.34 | 0.38 | 0.75 |
| 21 | 12422 | KV204_HUMAN | Ig kappa chain V-II region TEW | 0.74 | 1.29 | 0.74 | - | 0.74 | - | 0.74 | 0.74 |
| 22 | 188569 | CO3_HUMAN | Complement C3 | 0.68 | 0.44 | 0.19 | 0.24 | 0.29 | 0.06 | 0.56 | 0.68 |
| 23 | 40098 | FETUA_HUMAN | Alpha-2-HS-glycoprotein | 0.56 | 0.31 | 0.2 | 0.43 | 1.05 | 0.43 | 0.09 | 0.56 |

Figure 2I

| | | | | 0.94 | 1.21 | 0.22 | 1.21 | 0.7 | 1.52 | 0.39 | 0.49 |
|---|---|---|---|---|---|---|---|---|---|---|---|
| 24 | 54526 | VTDB_HUMAN | Vitamin D-binding protein | | | | | | | | |
| 25 | 54809 | A1BG_HUMAN | Alpha-1B-glycoprotein | 1.06 | 0.14 | 0.14 | 0.48 | 0.48 | 0.39 | 0.39 | 0.48 |
| 26 | 20064 | FRIL_HUMAN | Ferritin light chain | 1.01 | 0.19 | - | - | 0.19 | - | - | 0.42 |
| 27 | 266034 | FINC_HUMAN | Fibronectin | 0.71 | 0.16 | - | 0.55 | 0.18 | - | 0.09 | 0.41 |
| 28 | 11895 | KV106_HUMAN | Ig kappa chain V-I region EU | 0.78 | 0.78 | 0.33 | - | - | - | 0.33 | 0.33 |
| 29 | 12099 | KV101_HUMAN | Ig kappa chain V-I region AG | 0.76 | - | 0.33 | - | - | - | 0.33 | 0.33 |
| 30 | 12042 | LV302_HUMAN | Ig lambda chain V-III region LOI | 0.33 | 0.33 | - | 0.33 | 0.33 | 0.33 | 0.33 | 0.33 |
| 31 | 52385 | HEMO_HUMAN | Hemopexin | 0.86 | 0.32 | 0.41 | 0.62 | 0.51 | 0.73 | 0.62 | 0.32 |
| 32 | 39886 | AMBP_HUMAN | AMBP protein [Contains: Alpha-1-microglobulin] | 0.2 | 0.09 | 0.09 | 0.31 | 0.09 | - | - | 0.31 |
| 33 | 12681 | KV309_HUMAN | Ig kappa chain V-III region VG | 0.31 | 0.31 | 0.31 | 0.31 | 0.31 | - | 0.31 | 0.31 |
| 34 | 45861 | HPT_HUMAN | Haptoglobin [Contains: Haptoglobin alpha chain; Haptoglobin beta chain] | 3.1 | - | 3.1 | 1.37 | - | - | 2.51 | 0.27 |
| 35 | 47792 | AACT_HUMAN | Alpha-1-antichymotrypsin | 1.12 | 0.16 | 0.16 | 0.25 | 0.25 | 0.57 | 0.69 | 0.25 |
| 36 | 52106 | FIBG_HUMAN | Fibrinogen gamma chain | 1.46 | 1.14 | - | 0.07 | 0.07 | - | - | 0.23 |
| 37 | 95656 | FIBA_HUMAN | Fibrinogen alpha chain [Contains: Fibrinopeptide A] | 0.35 | 0.3 | - | - | 0.04 | - | - | 0.21 |
| 38 | 38486 | IGHA1_HUMAN | Ig alpha-1 chain C region | 1.54 | 1.31 | 1.31 | 0.92 | 0.1 | - | 0.2 | 0.2 |
| 39 | 21383 | FRIH_HUMAN | Ferritin heavy chain | 0.39 | - | - | - | - | - | - | 0.18 |
| 40 | 56577 | FIBB_HUMAN | Fibrinogen beta chain [Contains: Fibrinopeptide B] | 1.6 | 1.02 | - | - | - | - | - | 0.14 |
| 41 | 60510 | HRG_HUMAN | Histidine-rich glycoprotein | 0.2 | 0.06 | - | 0.13 | 0.06 | - | - | 0.13 |
| 42 | 28909 | CAH1_HUMAN | Carbonic anhydrase 1 | 0.28 | 0.28 | 0.64 | - | - | - | 0.28 | 0.13 |
| 43 | 42052 | ACTB_HUMAN | Actin, cytoplasmic 1 | 0.41 | 0.67 | 0.82 | - | - | 0.29 | 0.09 | 0.09 |
| 44 | 143654 | CFAH_HUMAN | Complement factor H | 0.16 | - | - | 0.19 | - | - | - | 0.08 |
| 45 | 103489 | ITIH4_HUMAN | Inter-alpha-trypsin inhibitor heavy chain H4 | 0.23 | 0.19 | 0.04 | 0.11 | 0.07 | - | 0.15 | 0.07 |

Figure 2J

| | | | | | | | | | | |
|---|---|---|---|---|---|---|---|---|---|---|
| 46 | 194247 | CO4A_HUMAN | Complement C4-A | 0.12 | 0.04 | - | - | 0.02 | - | 0.02 |
| 47 | 53031 | CLUS_HUMAN | Clusterin | 0.07 | 0.23 | - | 0.07 | 0.07 | 0.61 | 0.23 |
| 48 | 40022 | IDH3A_HUMAN | Isocitrate dehydrogenase [NAD] subunit alpha, mitochondrial | 0.09 | 0.09 | - | 0.09 | 0.09 | - | 0.09 |
| 49 | 23337 | RETBP_HUMAN | Plasma retinol-binding protein | 0.83 | - | - | 0.16 | 0.58 | 0.83 | 0.58 |
| 50 | 46484 | PEDF_HUMAN | Pigment epithelium-derived factor | 0.08 | 0.08 | - | 0.26 | 0.86 | 0.26 | - |
| 51 | 13671 | HV310_HUMAN | Ig heavy chain V-III region HIL | 0.29 | 0.29 | - | 0.29 | - | 0.29 | 0.59 |
| 52 | 12836 | HV320_HUMAN | Ig heavy chain V-III region GAL | 0.71 | - | - | 0.31 | 0.31 | 0.31 | 0.31 |
| 53 | 38747 | LUM_HUMAN | Lumican | 1.52 | - | - | 0.32 | 0.32 | - | 0.2 |
| 54 | 12462 | HV304_HUMAN | Ig heavy chain V-III region TIL | 0.32 | 0.74 | 0.32 | 0.32 | - | 0.32 | - |
| 55 | 12003 | LV102_HUMAN | Ig lambda chain V-I region HA | 0.33 | 0.33 | - | 0.33 | 0.33 | 0.33 | - |
| 56 | 39584 | APOH_HUMAN | Beta-2-glycoprotein 1 | 0.09 | 0.2 | - | 0.57 | 0.31 | - | 0.2 |
| 57 | 36431 | IGHG4_HUMAN | Ig gamma-4 chain C region | 1.42 | 0.99 | 0.8 | 0.99 | - | 0.99 | - |
| 58 | 53025 | ANT3_HUMAN | Antithrombin-III | 1.11 | 0.72 | 0.07 | 1.11 | 0.15 | 0.31 | 0.15 |
| 59 | 12746 | KV402_HUMAN | Ig kappa chain V-IV region Len | 0.71 | 0.71 | - | 1.24 | 1.24 | 1.24 | 0.71 |
| 60 | 66202 | LG3BP_HUMAN | Galectin-3-binding protein | 0.39 | - | - | - | - | - | 0.06 |
| 61 | 123407 | SDCG1_HUMAN | Serologically defined colon cancer antigen 1 | 0.03 | - | 0.3 | - | 0.03 | 0.03 | - |
| 62 | 13332 | HV305_HUMAN | Ig heavy chain V-III region BRO | 0.3 | 0.68 | - | - | 0.3 | - | - |
| 63 | 11768 | KV105_HUMAN | Ig kappa chain V-I region DEE | 0.34 | - | - | - | 0.79 | - | - |
| 64 | 55069 | VTNC_HUMAN | Vitronectin | 0.07 | - | - | 0.22 | - | 0.07 | - |
| 65 | 50210 | MUC_HUMAN | Ig mu chain C region | 0.43 | 1.54 | 0.15 | - | - | 0.15 | - |
| 66 | 70963 | AFAM_HUMAN | Afamin | 0.58 | 0.23 | - | 0.05 | - | 0.05 | - |

| | | | | | | | | | | | | |
|---|---|---|---|---|---|---|---|---|---|---|---|---|
| 67 | 23840 | TIMP1_HUMAN | Metalloproteinase inhibitor 1 | 0.16 | 0.16 | - | - | - | - | - | - | - |
| 68 | 165215 | PZP_HUMAN | Pregnancy zone protein | 0.07 | 0.05 | - | 0.12 | - | 0.1 | - | 0.09 | - |
| 69 | 72996 | KNG1_HUMAN | Kininogen-1 | 0.28 | 0.05 | - | - | 0.1 | 0.1 | 0.1 | 0.22 | - |
| 70 | 54873 | A2AP_HUMAN | Alpha-2-antiplasmin | 0.07 | - | - | 0.07 | - | - | - | - | - |
| 71 | 101782 | ITIH1_HUMAN | Inter-alpha-trypsin inhibitor heavy chain H1 | 0.11 | 0.07 | - | - | - | - | - | 0.24 | - |
| 72 | 16187 | HBG1_HUMAN | Hemoglobin subunit gamma-1 | 0.24 | - | - | - | - | - | - | - | - |
| 73 | 516666 | APOB_HUMAN | Apolipoprotein B-100 | 0.01 | - | - | - | - | - | - | - | - |
| 74 | 189923 | CO5_HUMAN | Complement C5 [Contains: Complement C5 beta chain; Complement C5 alpha chain; C5a anaphylatoxin; Complement C5 alpha~chain] | 0.02 | - | - | - | - | - | - | - | - |
| 75 | 108367 | CO6_HUMAN | Complement component C6 | 0.03 | - | - | - | - | - | - | - | - |
| 76 | 13114 | HV103_HUMAN | Ig heavy chain V-I region V35 | 0.3 | - | - | - | - | - | - | - | - |
| 77 | 11500 | LV301_HUMAN | Ig lambda chain V-III region SH | 0.81 | 0.81 | - | - | - | - | - | 0.34 | - |
| 78 | 12863 | KV310_HUMAN | Ig kappa chain V-III region VH | 0.31 | - | - | - | - | - | - | - | - |
| 79 | 80014 | TRFL_HUMAN | Lactotransferrin | 0.15 | 0.44 | - | - | - | - | - | - | - |
| 80 | 42829 | ILEU_HUMAN | Leukocyte elastase inhibitor | 0.09 | - | - | - | - | - | - | - | - |
| 81 | 8560 | UBIQ_HUMAN | Ubiquitin | - | - | - | - | - | - | - | - | - |
| 82 | 15123 | LEG7_HUMAN | Galectin-7 | - | - | - | - | - | - | - | - | - |
| 83 | 45037 | CATD_HUMAN | Cathepsin D | - | - | - | - | - | - | - | - | - |
| 84 | 27947 | CASPE_HUMAN | Caspase-14 | - | - | - | - | - | - | - | - | - |
| 85 | 59947 | CATA_HUMAN | Catalase | - | - | - | - | - | - | - | - | - |

| # | ID | Name | Description | | | | | | | |
|---|---|---|---|---|---|---|---|---|---|---|
| 86 | 37139 | APRV1_HUMAN | Retroviral-like aspartic protease 1 | - | - | - | - | - | - | - |
| 87 | 76926 | TGM3_HUMAN | Protein-glutamine gamma-glutamyltransferase E | - | - | - | - | - | - | - |
| 88 | 334021 | DESP_HUMAN | Desmoplakin | - | - | - | - | - | - | - |
| 89 | 105392 | OCRL_HUMAN | Inositol polyphosphate 5-phosphatase OCRL-1 | - | - | - | - | - | - | - |
| 90 | 82376 | PLAK_HUMAN | Junction plakoglobin | - | - | - | - | - | - | - |
| 91 | 112640 | NFH_HUMAN | Neurofilament heavy polypeptide | - | - | - | - | - | - | - |
| 92 | 115417 | PA24B_HUMAN | Cytosolic phospholipase A2 beta | - | - | - | - | - | - | - |
| 93 | 129242 | RPC2_HUMAN | DNA-directed RNA polymerase III subunit RPC2 | - | - | - | - | - | - | - |
| 94 | 199928 | RGPD5_HUMAN | RANBP2-like and GRIP domain-containing protein 5 | - | - | 0.18 | - | - | - | - |
| 95 | 43543 | MUCB_HUMAN | Ig mu heavy chain disease protein | - | 0.24 | - | - | - | - | - |
| 96 | 102013 | B3AT_HUMAN | Band 3 anion transport protein | - | 0.25 | - | - | - | - | - |
| 97 | 16389 | HV209_HUMAN | Ig heavy chain V-II region ARH-77 | - | - | - | - | - | - | - |
| 98 | 15684 | HBAZ_HUMAN | Hemoglobin subunit zeta | - | - | 5.92 | - | - | - | - |
| 99 | 13486 | KV401_HUMAN | Ig kappa chain V-IV region | - | - | - | - | - | - | - |
| 100 | 16159 | HBD_HUMAN | Hemoglobin subunit delta | - | - | 0.24 | - | - | 0.54 | - |
| 101 | 16249 | HBE_HUMAN | Hemoglobin subunit epsilon | - | - | - | - | - | 0.24 | - |
| 102 | 11810 | KV104_HUMAN | Ig kappa chain V-I region CAR | - | - | - | 0.34 | - | - | - |
| 103 | 12931 | KV110_HUMAN | Ig kappa chain V-I region HK102 | - | - | - | 0.31 | - | - | - |

Figure 2M

| | | | | | | | | | | |
|---|---|---|---|---|---|---|---|---|---|---|
| 104 | 53406 | ANGT_HUMAN | Angiotensinogen | - | - | - | - | 0.07 | 0.14 | - | - |
| 105 | 38777 | FHR1_HUMAN | Complement factor H-related protein 1 | - | - | - | - | - | - | - | 0.1 |
| 106 | 84583 | CO2_HUMAN | Complement C2 | - | - | - | - | - | - | - | 0.04 |
| 107 | 45371 | APOA4_HUMAN | Apolipoprotein A-IV | - | 0.17 | - | 2.84 | 1.59 | - | 3.16 | 0.61 |
| 108 | 11889 | KV116_HUMAN | Ig kappa chain V-I region Roy | - | 0.78 | - | 0.78 | - | - | - | - |
| 109 | 12745 | HV303_HUMAN | Ig heavy chain V-III region VH26 | - | - | - | 0.71 | - | - | - | - |
| 110 | 11192 | PLGB_HUMAN | Plasminogen-related protein B | - | - | - | 0.36 | - | - | - | - |
| 111 | 11715 | KV119_HUMAN | Ig kappa chain V-I region Wes | - | - | - | 0.34 | - | - | - | - |
| 112 | 11941 | KV113_HUMAN | Ig kappa chain V-I region Lay | - | 0.33 | 0.33 | 0.33 | 0 | 0.33 | 0.33 | 0.33 |
| 113 | 86847 | CFAB_HUMAN | Complement factor B | - | - | - | 0.13 | 0.18 | - | - | - |
| 114 | 68072 | CFAI_HUMAN | Complement factor I | - | 0.05 | - | 0.11 | - | - | - | 0.05 |
| 115 | 36246 | APOE_HUMAN | Apolipoprotein E | - | - | - | 0.1 | - | - | 0.22 | 0.1 |
| 116 | 39895 | PON1_HUMAN | Serum paraoxonase/arylesterase 1 | - | - | - | - | - | - | 0.2 | - |
| 117 | 11624 | LV403_HUMAN | Ig lambda chain V-IV region Hil | - | - | - | - | - | - | 0.34 | - |
| 118 | 21547 | APOD_HUMAN | Apolipoprotein D | - | - | - | - | - | - | 0.18 | - |
| 119 | 86043 | GELS_HUMAN | Gelsolin | - | - | - | 0.04 | - | - | - | - |
| 120 | 96650 | CO7_HUMAN | Complement component C7 | - | - | - | 0.3 | - | - | - | 0.04 |
| 121 | 12782 | KV201_HUMAN | Ig kappa chain V-II region Cum | - | - | - | 0.31 | - | 0.31 | - | - |
| 122 | 93247 | PLMN_HUMAN | Plasminogen | - | - | - | 0.48 | 0.21 | 0.12 | 0.08 | - |
| 123 | 16041 | IGJ_HUMAN | Immunoglobulin J chain | - | 0.54 | 0.24 | - | - | - | - | 0.24 |
| 124 | 11752 | CO005_HUMAN | Uncharacterized protein C15orf5 | - | - | - | - | - | - | - | - |

Figure 2N

| | | | | | | | | | | |
|---|---|---|---|---|---|---|---|---|---|---|
| 125 | 13059 | HV313_HUMAN | Ig heavy chain V-III region POM | - | - | - | - | - | - | - |
| 126 | 34454 | FCN2_HUMAN | Ficolin-2 | - | - | - | - | - | - | - |
| 127 | 40624 | RAI3_HUMAN | Retinoic acid-induced protein 3 | - | - | - | - | - | - | - |
| 128 | 61187 | CH60_HUMAN | 60 kDa heat shock protein, mitochondrial | - | - | - | 0 | | - | - |
| 129 | 58259 | MMSA_HUMAN | Methylmalonate-semialdehyde dehydrogenase [acylating], mitochondrial | - | - | - | - | - | - | - |
| 130 | 69484 | EZRI_HUMAN | Ezrin | - | - | - | - | - | - | - |
| 131 | 596494 | FCGBP_HUMAN | IgGFc-binding protein | - | - | - | - | 0.02 | - | - |
| 132 | 168870 | MRC1_HUMAN | Macrophage mannose receptor 1 | - | - | - | - | - | - | - |
| 133 | 514737 | APOA_HUMAN | Apolipoprotein(a) | - | - | - | - | - | - | - |
| 134 | 59703 | K1C10_HUMAN | Keratin, type I cytoskeletal 10 | 1.19 | 4.43 | 0.83 | 0.2 | 1.19 | 0.94 | 2.78 |
| 135 | 51875 | K1C14_HUMAN | Keratin, type I cytoskeletal 14 | 0.42 | 0.87 | 0.15 | 0.15 | 0.15 | 0.23 | 0.32 |
| 136 | 44065 | K1C19_HUMAN | Keratin, type I cytoskeletal 19 | 0.77 | - | 0.18 | 0.18 | - | 0.28 | 0.18 |
| 137 | 53671 | K2C8_HUMAN | Keratin, type II cytoskeletal 8 | 0.31 | 0.22 | 0.07 | - | 0.07 | 0.4 | 0.07 |

Figure 20

| Cyst # | 15 | 6 | 8 | 10 | 1 | 2 | 4 | 16 | 18 | 13 | 7 | 11 | 17 | 14 | 9 | 19A | 19B | 12 | 5 | 3 | 21 |
|---|---|---|---|---|---|---|---|---|---|---|---|---|---|---|---|---|---|---|---|---|---|
| Histology | | | | | | | | | | | | | IPMN adenoma | MCA | | | IPMN adenoma | | Adeno-carcinoma | | MCA |
| CEA | - | - | - | - | <0.1 | 2 | 49 | 61 | 176 | 182 | 231 | 333 | 410 | 582 | 797 | 2853 | - | 5115 | 14175 | 63830 | - |
| Alpha-amylase 2B | | | | | | | 4.0 | 3.2 | 2.5 | 2.7 | 2.1 | 1.5 | 2.1 | | 2.7 | 1.2 | | 1.0 | | | |
| Pancreatic alpha-amylase | | | 0.2 | 0.2 | | | 4.0 | 3.1 | 2.7 | 2.7 | 2.2 | 1.5 | 2.2 | 0.7 | 2.7 | 1.4 | 0.3 | 1.1 | | | |
| Pancreatic secretory granule membrane major glycoprotein GP2 | | | | | | | 0.6 | 0.6 | 0.7 | 0.6 | 0.4 | 0.5 | 0.4 | 0.4 | 0.5 | 0.4 | | 0.2 | | | |
| Pancreatic triacylglycerol lipase | | | | | | | 0.3 | 0.5 | | 0.7 | 1.6 | 1.8 | 0.6 | 0.7 | 1.5 | 2.5 | 0.2 | 0.2 | | 0.6 | |
| Bile salt-activated lipase | | | | | | | | | 0.3 | 0.3 | 0.5 | 1.0 | 0.1 | | 0.5 | 0.8 | 0.2 | | | | |
| Phospholipase A2 | | | | | | | 0.2 | 0.9 | 0.2 | 0.5 | 0.5 | 0.9 | 0.5 | 0.1 | 0.2 | 0.9 | | 0.2 | | | |
| Colipase | | | | | | | | | 0.3 | 0.7 | | 1.3 | | | | 2.0 | | | | | |
| Carboxypeptidase A1 | | | | | | | 4.0 | 0.5 | 3.0 | 3.0 | 3.3 | 3.3 | 0.7 | 0.4 | 3.6 | 1.7 | 0.5 | 0.8 | | 0.6 | |
| Carboxypeptidase A2 | | | | | | | 1.7 | 0.8 | 0.3 | 1.2 | 1.3 | 1.2 | 0.1 | | 1.7 | 1.0 | 0.1 | 0.2 | | 0.7 | |
| Carboxypeptidase B | | | | | | | 5.6 | 1.7 | 4.3 | 5.1 | 5.6 | 5.1 | 1.1 | 0.5 | 6.7 | 2.3 | 0.6 | 1.7 | | 1.0 | |
| Chymotrypsinogen B2 | | | | | | | 0.5 | 0.9 | 1.1 | 0.5 | 0.3 | 0.7 | 0.3 | | 0.5 | 0.9 | | 0.7 | | 0.7 | |
| Chymotrypsinogen B | | | | | | | | | 0.9 | | 0.3 | | | 0.3 | | | | | | 0.3 | |
| Chymotrypsin-C | | | | | | | 0.6 | 0.8 | 1.6 | 0.8 | 0.8 | 0.8 | 0.8 | 0.1 | 0.8 | 0.8 | 0.6 | 0.6 | | | |
| Elastase-2A | | | | | | | 2.8 | 1.6 | 2.4 | 1.6 | 1.3 | 1.6 | 0.3 | | 2.4 | 0.6 | 0.6 | 0.4 | | | |
| Elastase-2B | | | | | | | 0.6 | 0.4 | 0.4 | 0.4 | 0.6 | 0.6 | 0.3 | 0.1 | 0.6 | | 0.1 | | | | |
| Elastase-3A | | | 0.1 | | | | 3.7 | 3.1 | 3.1 | 2.7 | 2.7 | 2.7 | 2.7 | | 3.7 | 1.6 | | | | 1.3 | |
| Elastase-3B | | | | | | | 1.9 | 1.1 | 1.6 | 1.6 | 0.8 | 1.1 | 1.3 | | 1.3 | 1.1 | | | | 0.4 | |
| Lithostathine 1 alpha | | | | | | | 0.4 | | 2.0 | 0.4 | 0.4 | 1.1 | 0.2 | | 0.7 | 1.1 | | 1.5 | | 1.5 | |
| Trypsin-1 | | | | | 0.1 | | 1.2 | 0.5 | 1.9 | 0.7 | 0.9 | 1.2 | 0.9 | 0.5 | 1.5 | 0.7 | 0.7 | 1.2 | | 0.9 | |
| Trypsin-2 | | | | | | | 0.5 | 0.7 | 1.2 | 0.7 | 0.7 | 1.2 | 0.3 | 0.7 | 0.9 | 0.5 | 0.5 | 0.3 | | 1.5 | |
| Trypsin-3 | | | | | | | 0.2 | 0.2 | 0.5 | 0.2 | 0.2 | 0.4 | 0.2 | | 0.5 | 0.7 | 0.2 | 0.1 | | 0.4 | |
| Kallikrein-1 | | | | | | | | 0.1 | 0.1 | 0.3 | | 0.1 | 0.3 | | 0.3 | 0.1 | | | | | |

Table 3. Pancreatic enzyme proteins in the pancreatic cyst samples. Legends are the same as for Table 2.

Figure 3

| Cyst # | 15 | 6 | 8 | 10 | 1 | 2 | 4 | 16 | 18 | 13 | 7 | 11 | 17 | 14 | 9 | 19A | 19B | 12 | 5 | 3 | 21 |
|---|---|---|---|---|---|---|---|---|---|---|---|---|---|---|---|---|---|---|---|---|---|
| Histology | | | | | | | | | | | | | IPMN adenoma | MCA | | | IPMN adenoma | | Adeno-carcinoma | | MCA |
| CEA | - | - | - | - | <0.1 | 2 | 49 | 61 | 176 | 182 | 231 | 333 | 410 | 582 | 797 | 2853 | - | 5115 | 14175 | 63830 | - |
| Mucin-1 | | | | | | | | | | | | | | 0.06 | | | 0.06 | 0.03 | | 0.16 | |
| Mucin-2 | | | | | | | | | | | | | | | | 0.01 | 0.01 | 0.01 | | | |
| Mucin-5AC | | | | | | | | | | | | | 0.01 | | | | | | | | |
| Mucin-5B | | | | | | | | | | | 0.06 | 0.03 | 0.24 | | 0.14 | 0.11 | 0.27 | 0.21 | | 0.21 | |
| Mucin-6 | | | | | | 0.07 | | | | | | | 0.02 | 0.21 | | 0.01 | 0.01 | 0.02 | | 0.02 | |
| CEACAM1 | | | | | | | | | 0.06 | | | | 0.01 | 0.03 | | 0.06 | 0.14 | 0.04 | | 0.10 | |
| CEACAM5 (CEA) | | | | | | | | | 0.05 | | | | | 0.05 | 0.05 | 0.15 | 0.15 | | 0.06 | | |
| CEACAM6 | | | | | | | | | | | | | | 0.10 | | | 0.10 | | 0.10 | 0.26 | |
| CEACAM7 | | | | | | | | | | | | | | 0.13 | | | | | | 0.33 | |
| CEACAM8 | | | | | | | | | 0.10 | | | | | 0.10 | | | 0.10 | | | 0.10 | 0.10 |
| Protein S100-A6 | | | 0.94 | | | | | | | | | | | | | | 0.39 | | 0.39 | | 0.39 |
| Protein S100-A8 | | | | | | | | 0.37 | | | | | | 1.56 | | | | | 5.54 | | 2.50 |
| Protein S100-A9 | | | | | | | | 0.68 | | | | | | 0.68 | | | | | 3.73 | | 2.65 |
| Protein S100-A11 | | | | | | | | | | | | | | | | | | | 1.37 | | 0.33 |

Table 4. Proteomic potential biomarkers for mucins, CEACAMs, and S100s found in the pancreatic cyst samples. Legends are the same as for Table 2.

Figure 4

BIOMARKERS FOR THE DIAGNOSIS AND TREATMENT OF PANCREATIC CANCER

This application is a divisional of U.S. application Ser. No. 12/812,394 filed 18 Aug. 2010, which is a §371 application of PCT/US09/31587 filed 21 Jan. 2009 which in turn claims priority to U.S. Provisional Application 61/021,772 filed 17 Jan. 2008, the entire contents of each being incorporated by reference herein.

Pursuant to 35 U.S.C. §202(c) it is acknowledged that the U.S. Government has certain rights in the invention described, which was made in part with funds from the National Institutes of Health, Grant Number, CA119242.

FIELD OF THE INVENTION

This invention relates to the fields of oncology and proteomic analysis. More specifically, the invention discloses biomarkers that are present in pancreatic cyst fluid which are indicative of an increased risk for the development of pancreatic cancer and methods of use thereof in diagnostic and prognostic assays. Also disclosed are screening assays utilizing the biomarkers of the invention to identify agents useful for the treatment of pancreatic cancer.

BACKGROUND OF THE INVENTION

Several publications and patent documents are cited throughout the specification in order to describe the state of the art to which this invention pertains. Each of these citations is incorporated herein by reference as though set forth in full.

Increasing use of high resolution computerized tomography and magnetic resonance imaging in clinical practice has resulted in detection of a growing number of pancreatic cysts (1). As a result, clinicians are frequently asked to determine the biological nature of these cystic lesions, and to make treatment recommendations accordingly. However, there are currently no diagnostic indicators that are consistently reliable, obtainable, and conclusive for diagnosing and risk-stratifying pancreatic cysts. The sensitivity of pancreatic cyst fluid cytology has been reported as only 27-64% in most series. Several studies have suggested that a variety of tumor markers (e.g., CEA(2), CA 19-9, CA 15-3) may distinguish mucinous from non-mucinous cystic lesions, and also may predict whether a cyst harbors areas of malignant transformation (3-5).

The biologic nature and histopathologic features of pancreatic cysts are varied (3, 6). Ten to twenty percent of pancreatic cysts are neoplastic, including neoplasms which grow as cystic structures (i.e., primary cystic neoplasms of the pancreas), and solid neoplasms that have undergone cystic degeneration. Serous cystadenomas (microcystic adenomas) account for approximately 32-39% of the primary cystic neoplasms and have very low malignant potential. Mucinous cystic neoplasms, which include mucinous cystadenomas and intraductal papillary mucinous neoplasms, are a subgroup of primary cystic neoplasms that have malignant potential. Nomenclature describing the evolution of these lesions, from benign to malignant, is provided elsewhere (7, 8). Mucinous cystic neoplasms and intraductal papillary mucinous neoplasms (IPMNs) account for approximately 10-45% and 21-33% of primary cystic neoplasms, respectively (6, 9-11). Two subtypes of IPMN have been described (1, 12), a main duct variant and a branch duct variant; the latter may have a more indolent course. There are other less common forms of primary cystic neoplasms of the pancreas, such as solid pseudopapillary tumors.

In the absence of reliable methods of quantifying the malignant potential of a suspected pre-malignant cystic neoplasm of the pancreas, if existing clinical parameters suggest the presence of one such lesion in a person that is otherwise an acceptable surgical risk, partial or total pancreatomy may be recommended but can result in significant morbidity and mortality (13). Alternatively, a conservative "watch-and-wait" approach (i.e., serial imaging over time) is advocated for some patients, but this strategy may be suboptimal due to incremental costs accrued during surveillance, and the possibility that malignant transformation may occur between surveillance time points.

In light of all the foregoing, it is clear that a more reliable method for identifying those patients at increased risk for developing pancreatic cancer is urgently needed.

SUMMARY OF THE INVENTION

In accordance with the present invention, a method of diagnosing an increased risk for the development of pancreatic cancer in a human test subject is provided. An exemplary method entails isolating a pancreatic cyst fluid specimen from the subject; analyzing the fluid specimen for the presence of at least three biomarkers associated with increased risk of pancreatic carcinoma, wherein the presence of said biomarkers is indicative of an increased risk for pancreatic cancer, said biomarkers being selected from the group consisting of mucin 1, mucin 2, mucin 5AC, mucin 5B, mucin 6, CEA CAM 1, CEACAM 6, CEACAM 7, CEACAM 8, S100-A6, S100-A8, S100 A9 and S100 A-11.

The risk of pancreatic cancer increases when the proteomic analysis shows an increase in several combinations of biomarkers. These are as follows: a) the presence of several isoforms of mucins e.g., mucin 1, 2, 5AC, 5B, and 6; b) the presence of both mucins and certain isoforms of CEA, including CEACAM 1, 6, 7, and 8; and c) mucins and CEA are variable but CEACAM8 is present and at least two of S100-A6, A8, A9, or A11 are present.

Also provided is a solid support comprising antibodies which are immunospecific for the biomarkers described above. Such supports can include, without limitation, filters, biacore chips, ELISA plates and the like.

BRIEF DESCRIPTION OF THE DRAWINGS

FIG. 1 is a table providing clinical information for the pancreatic cyst fluid samples tested herein. CEA (ng/mL) and Amylase (units/mL) are results from clinical lab immuno assays. MCA=mucinous cystadenoma. Cytology categories: A—Benign: No evidence of benign mucinous epithelium, atypical cells or carcinoma. C—Atypical/suspicious cytology.

FIGS. 2A-2O provide tables showing representatives of 137 plasma proteins distributed among the pancreatic cyst samples. The numbers presented in FIG. 2A are emPAI scores which are roughly proportional to protein abundance. Dark (>1), medium (0.1 to 1), and light (<0.1) shading denotes relative protein abundance. No proteins were detected for the empty boxes. CEA=ng/mL.

FIG. 3 is a table listing the pancreatic enzyme proteins in the pancreatic cyst samples. Legends are the same as for FIG. 2.

FIG. 4 is a table listing proteomic biomarkers for pancreatic cancer e.g., mucins, CEACAMs, and S100s found in the pancreatic cyst samples. Legends are the same as for FIG. 2.

DETAILED DESCRIPTION OF THE INVENTION

There are currently no diagnostic indicators that are consistently reliable, obtainable, and conclusive for diagnosing and risk-stratifying pancreatic cysts. To establish more effective diagnostic biomarkers and to provide deeper understanding about the molecular profile within these cysts, we identified and quantified about 500 cyst fluid proteins and correlated the findings to clinical parameters, when available. Pancreatic cyst fluids were collected by endoscopic ultrasound-guided fine needle aspiration (EUS-FNA) from 20 patients. The proteins in the cyst fluids were ascertained by LC/MS/MS analysis of every gel slice from 1 D gel fractionation of each sample, using partial peptide sequencing on a highly accurate and stable mass spectrometer. Measurements of traditional markers of mucins, amylase, and CEA were obtained simultaneously from 15 micrograms of protein from less than 40 microliters of cyst fluids per sample. The proteomic techniques utilized provided comprehensive information about pancreatic enzymes, plasma infiltrate proteins, and proteins that may have been produced by the pancreas epithelium. Our data suggest that diagnosis based upon the proteome of pancreatic cyst fluid may include the expression of two homologs of amylase, five mucins, five CEA-related cell adhesion molecules (CEACAMs), and four S100 homologs. Furthermore, our study indicates that proteomic profiling using small amounts of cyst fluids can be a valuable tool for diagnosing and risk-stratifying cystic lesions of the pancreas.

Bodily fluids aspired from pancreatic cysts contain hundreds of different proteins. Some of the proteins are natural pancreatic enzyme secretions; others are plasma derived; yet others may be released by the cyst epithelium either normally or as a result of cellular transformation. Proteomics by mass spectrometry provide a means to quickly quantify hundreds of these proteins simultaneously from a small volume of fluids. The identification of proteins that change their levels upon cellular transformation provides biomarkers for pancreas malignancy.

We have determined that the risk of pancreatic cancer increases when the proteomic analysis shows an increase in several combinations of biomarkers: (1) When several isoforms of mucins 1, 2, 5AC, 5B, and 6 are present; (2) when mucins are present, the risk further increases when isoforms of CEA, including CEACAM 1, 6, 7, and 8 are present; (3) when mucins and CEA are either present or absent, the risk increases when CEACAM8 is present and when certain of the biomarkers S100-A6, A8, A9, or A11 are present.

The biomarkers of the invention include genes and proteins, and variants and fragments thereof. Such biomarkers include DNA comprising the entire or partial sequence of the nucleic acid sequence encoding the biomarker, or the complement of such a sequence. The biomarker nucleic acids also include RNA comprising the entire or partial sequence of any of the nucleic acid sequences of interest. A biomarker protein is a protein encoded by or corresponding to a DNA biomarker of the invention. A biomarker protein comprises the entire or partial amino acid sequence of any of the biomarker proteins or polypeptides.

A "biomarker" is any gene or protein whose level of expression in a tissue or cell is altered compared to that of a normal or healthy cell or tissue. Biomarkers of the invention are selective for underlying risk of progression to pancreatic cancer. By "selectively overexpressed in pancreatic cyst fluid" is intended that the biomarker of interest is overexpressed in neoplastic cysts relative to benign or non-malignant cysts. Thus, detection of the biomarkers of the invention permits the differentiation of samples indicative of increased risk of developing neoplasms of the pancreas from samples that are indicative of benign proliferation. Representative biomarkers for pancreatic cell transformation include one or more or a plurality of the following proteins:

Mucin-5B precursor—*Homo sapiens* (Human)
Mucin-5AC—*Homo sapiens* (Human)
Mucin-1 precursor—*Homo sapiens* (Human)
Gelsolin precursor—*Homo sapiens* (Human)
Carcinoembryonic antigen-related cell adhesion molecule 5 precursor—*Homo sapiens* (Human)
Ezrin—*Homo sapiens* (Human)
Galectin-3-binding protein precursor—*Homo sapiens* (Human)
Mucin-13 precursor—*Homo sapiens* (Human)
Leukocyte elastase inhibitor—*Homo sapiens* (Human)
Annexin A1—*Homo sapiens* (Human)
Annexin A2—*Homo sapiens* (Human)
Carcinoembryonic antigen-related cell adhesion molecule 6 precursor—*Homo sapiens* (Human)
Annexin A3—*Homo sapiens* (Human)
Annexin A4—*Homo sapiens* (Human)
Galectin-4—*Homo sapiens* (Human)
Annexin A5—*Homo sapiens* (Human)
Phosducin—*Homo sapiens* (Human)
Tetraspanin-8—*Homo sapiens* (Human)
Galectin-3—*Homo sapiens* (Human)
Neutrophil gelatinase-associated lipocalin precursor—*Homo sapiens* (Human)
Anterior gradient protein 2 homolog precursor—*Homo sapiens* (Human)
Protein S100-A11—*Homo sapiens* (Human)
Protein S100-A6—*Homo sapiens* (Human)
Protein S100-A8—*Homo sapiens* (Human)
Protein S100-A9—*Homo sapiens* (Human Expression of the biomarkers described herein is indicative of cyst fluid protein profiles that are associated with benign pancreatic disease, pre-malignancy, and neoplastic lesions of the pancreas.

The phrase "genetic signature" refers to a plurality of nucleic acid molecules whose expression levels are indicative of a given metabolic or pathological state. The genetic signatures described herein can be employed to characterize at the molecular level the condition of the pancreatic cyst that is associated with an increased risk of pancreatic cancer, thus providing a useful molecular tool for predicting outcomes, for identifying patients at risk, and for use in biomarker in assays for evaluating cancer preventive agents.

For purposes of the present invention, "a" or "an" entity refers to one or more of that entity; for example, "a cDNA" refers to one or more cDNA or at least one cDNA. The terms "a" or "an," "one or more" and "at least one" can be used interchangeably herein. It is also noted that the terms "comprising," "including," and "having" can be used interchangeably. Furthermore, a compound "selected from the group consisting of" refers to one or more of the compounds in the list that follows, including mixtures (i.e. combinations) of two or more of the compounds. According to the present invention, an isolated, or biologically pure molecule is a compound that has been removed from its natural milieu. As such, "isolated" and "biologically pure" do not necessarily reflect the extent to which the compound has been purified. An isolated compound of the present invention can be obtained from its natural source, can be produced using laboratory synthetic techniques or can be produced by any such chemical synthetic route.

The term "genetic alteration" as used herein refers to a change from the wild-type or reference sequence of one or more nucleic acid molecules. Genetic alterations include without limitation, base pair substitutions, additions and deletions of at least one nucleotide from a nucleic acid molecule of known sequence.

The term "solid matrix" as used herein refers to any format, such as beads, microparticles, a microarray, the surface of a microtitration well or a test tube, a dipstick or a filter. The material of the matrix may be polystyrene, cellulose, latex, nitrocellulose, nylon, polyacrylamide, dextran or agarose.

"Sample" or "patient sample" or "biological sample" generally refers to a sample which may be tested for a particular molecule, preferably a genetic signature specific marker molecule, such as a marker shown in the tables provided below. Samples may include but are not limited to cells, cyst fluids, body fluids, including blood, serum, plasma, urine, saliva, tears, pleural fluid and the like.

The phrase "consisting essentially of" when referring to a particular nucleotide or amino acid means a sequence having the properties of a given SEQ ID NO. For example, when used in reference to an amino acid sequence, the phrase includes the sequence per se and molecular modifications that would not affect the functional and novel characteristics of the sequence.

With regard to nucleic acids used in the invention, the term "isolated nucleic acid" is sometimes employed. This term, when applied to DNA, refers to a DNA molecule that is separated from sequences with which it is immediately contiguous (in the 5' and 3' directions) in the naturally occurring genome of the organism from which it was derived. For example, the "isolated nucleic acid" may comprise a DNA molecule inserted into a vector, such as a plasmid or virus vector, or integrated into the genomic DNA of a prokaryote or eukaryote. An "isolated nucleic acid molecule" may also comprise a cDNA molecule. An isolated nucleic acid molecule inserted into a vector is also sometimes referred to herein as a recombinant nucleic acid molecule.

With respect to RNA molecules, the term "isolated nucleic acid" primarily refers to an RNA molecule encoded by an isolated DNA molecule as defined above. Alternatively, the term may refer to an RNA molecule that has been sufficiently separated from RNA molecules with which it would be associated in its natural state (i.e., in cells or tissues), such that it exists in a "substantially pure" form. By the use of the term "enriched" in reference to nucleic acid it is meant that the specific DNA or RNA sequence constitutes a significantly higher fraction (2-5 fold) of the total DNA or RNA present in the cells or solution of interest than in normal cells or in the cells from which the sequence was taken. This could be caused by a person by preferential reduction in the amount of other DNA or RNA present, or by a preferential increase in the amount of the specific DNA or RNA sequence, or by a combination of the two. However, it should be noted that "enriched" does not imply that there are no other DNA or RNA sequences present, just that the relative amount of the sequence of interest has been significantly increased.

It is also advantageous for some purposes that a nucleotide sequence be in purified form. The term "purified" in reference to nucleic acid does not require absolute purity (such as a homogeneous preparation); instead, it represents an indication that the sequence is relatively purer than in the natural environment (compared to the natural level, this level should be at least 2-5 fold greater, e.g., in terms of mg/ml). Individual clones isolated from a cDNA library may be purified to electrophoretic homogeneity. The claimed DNA molecules obtained from these clones can be obtained directly from total DNA or from total RNA. The cDNA clones are not naturally occurring, but rather are preferably obtained via manipulation of a partially purified naturally occurring substance (messenger RNA). The construction of a cDNA library from mRNA involves the creation of a synthetic substance (cDNA) and pure individual cDNA clones can be isolated from the synthetic library by clonal selection of the cells carrying the cDNA library. Thus, the process which includes the construction of a cDNA library from mRNA and isolation of distinct cDNA clones yields an approximately $10^{-6}$-fold purification of the native message. Thus, purification of at least one order of magnitude, preferably two or three orders, and more preferably four or five orders of magnitude is expressly contemplated. Thus, the term "substantially pure" refers to a preparation comprising at least 50-60% by weight the compound of interest (e.g., nucleic acid, oligonucleotide, etc.). More preferably, the preparation comprises at least 75% by weight, and most preferably 90-99% by weight, the compound of interest. Purity is measured by methods appropriate for the compound of interest.

The term "complementary" describes two nucleotides that can form multiple favorable interactions with one another. For example, adenine is complementary to thymine as they can form two hydrogen bonds. Similarly, guanine and cytosine are complementary since they can form three hydrogen bonds. Thus if a nucleic acid sequence contains the following sequence of bases, thymine, adenine, guanine and cytosine, a "complement" of this nucleic acid molecule would be a molecule containing adenine in the place of thymine, thymine in the place of adenine, cytosine in the place of guanine, and guanine in the place of cytosine. Because the complement can contain a nucleic acid sequence that forms optimal interactions with the parent nucleic acid molecule, such a complement can bind with high affinity to its parent molecule.

With respect to single stranded nucleic acids, particularly oligonucleotides, the term "specifically hybridizing" refers to the association between two single-stranded nucleotide molecules of sufficiently complementary sequence to permit such hybridization under pre-determined conditions generally used in the art (sometimes termed "substantially complementary"). In particular, the term refers to hybridization of an oligonucleotide with a substantially complementary sequence contained within a single-stranded DNA or RNA molecule of the invention, to the substantial exclusion of hybridization of the oligonucleotide with single-stranded nucleic acids of non-complementary sequence. For example, specific hybridization can refer to a sequence which hybridizes to any specific marker gene or nucleic acid, but does not hybridize to other human nucleotides. Also polynucleotide which "specifically hybridizes" may hybridize only to a specific marker, such a genetic signature-specific marker shown in the Tables below. Appropriate conditions enabling specific hybridization of single stranded nucleic acid molecules of varying complementarity are well known in the art.

For instance, one common formula for calculating the stringency conditions required to achieve hybridization between nucleic acid molecules of a specified sequence homology is set forth below (Sambrook et al., *Molecular Cloning*, Cold Spring Harbor Laboratory (1989):

$$T_m = 81.5° C. + 16.6 \text{ Log }[Na+] + 0.41 \text{ (\% } G+C) - 0.63(\% \text{ formamide}) - 600/\#bp \text{ in duplex}$$

As an illustration of the above formula, using [Na+]= [0.368] and 50% formamide, with GC content of 42% and an average probe size of 200 bases, the $T_m$ is 57° C. The $T_m$ of a DNA duplex decreases by 1-1.5° C. with every 1% decrease in homology. Thus, targets with greater than about 75% sequence identity would be observed using a hybridization temperature of 42° C.

The stringency of the hybridization and wash depend primarily on the salt concentration and temperature of the solutions. In general, to maximize the rate of annealing of the probe with its target, the hybridization is usually carried out at salt and temperature conditions that are 20-25° C. below the calculated $T_m$ of the hybrid. Wash conditions should be as stringent as possible for the degree of identity of the probe for the target. In general, wash conditions are selected to be approximately 12-20° C. below the $T_m$ of the hybrid. In regards to the nucleic acids of the current invention, a moderate stringency hybridization is defined as hybridization in 6×SSC, 5×Denhardt's solution, 0.5% SDS and 100 µg/ml denatured salmon sperm DNA at 42° C., and washed in 2×SSC and 0.5% SDS at 55° C. for 15 minutes. A high stringency hybridization is defined as hybridization in 6×SSC, 5×Denhardt's solution, 0.5% SDS and 100 µg/ml denatured salmon sperm DNA at 42° C., and washed in 1×SSC and 0.5% SDS at 65° C. for 15 minutes. A very high stringency hybridization is defined as hybridization in 6×SSC, 5×Denhardt's solution, 0.5% SDS and 100 µg/ml denatured salmon sperm DNA at 42° C., and washed in 0.1× SSC and 0.5% SDS at 65° C. for 15 minutes.

The term "oligonucleotide" or "oligo" as used herein means a short sequence of DNA or DNA derivatives typically 8 to 35 nucleotides in length, primers, or probes. An oligonucleotide can be derived synthetically, by cloning or by amplification. An oligo is defined as a nucleic acid molecule comprised of two or more ribo- or deoxyribonucleotides, preferably more than three. The exact size of the oligonucleotide will depend on various factors and on the particular application and use of the oligonucleotide. The term "derivative" is intended to include any of the above described variants when comprising an additional chemical moiety not normally a part of these molecules. These chemical moieties can have varying purposes including, improving solubility, absorption, biological half life, decreasing toxicity and eliminating or decreasing undesirable side effects.

The term "probe" as used herein refers to an oligonucleotide, polynucleotide or nucleic acid, either RNA or DNA, whether occurring naturally as in a purified restriction enzyme digest or produced synthetically, which is capable of annealing with or specifically hybridizing to a nucleic acid with sequences complementary to the probe. A probe may be either single-stranded or double-stranded. The exact length of the probe will depend upon many factors, including temperature, source of probe and use of the method. For example, for diagnostic applications, depending on the complexity of the target sequence, the oligonucleotide probe typically contains 15-25 or more nucleotides, although it may contain fewer nucleotides. The probes herein are selected to be complementary to different strands of a particular target nucleic acid sequence. This means that the probes must be sufficiently complementary so as to be able to "specifically hybridize" or anneal with their respective target strands under a set of pre-determined conditions. Therefore, the probe sequence need not reflect the exact complementary sequence of the target. For example, a non-complementary nucleotide fragment may be attached to the 5' or 3' end of the probe, with the remainder of the probe sequence being complementary to the target strand. Alternatively, non-complementary bases or longer sequences can be interspersed into the probe, provided that the probe sequence has sufficient complementarity with the sequence of the target nucleic acid to anneal therewith specifically.

The term "primer" as used herein refers to an oligonucleotide, either RNA or DNA, either single-stranded or double-stranded, either derived from a biological system, generated by restriction enzyme digestion, or produced synthetically which, when placed in the proper environment, is able to functionally act as an initiator of template-dependent nucleic acid synthesis. When presented with an appropriate nucleic acid template, suitable nucleoside triphosphate precursors of nucleic acids, a polymerase enzyme, suitable cofactors and conditions such as a suitable temperature and pH, the primer may be extended at its 3' terminus by the addition of nucleotides by the action of a polymerase or similar activity to yield a primer extension product. The primer may vary in length depending on the particular conditions and requirement of the application. For example, in diagnostic applications, the oligonucleotide primer is typically 15-25 or more nucleotides in length. The primer must be of sufficient complementarity to the desired template to prime the synthesis of the desired extension product, that is, to be able anneal with the desired template strand in a manner sufficient to provide the 3' hydroxyl moiety of the primer in appropriate juxtaposition for use in the initiation of synthesis by a polymerase or similar enzyme. It is not required that the primer sequence represent an exact complement of the desired template. For example, a non-complementary nucleotide sequence may be attached to the 5' end of an otherwise complementary primer. Alternatively, non-complementary bases may be interspersed within the oligonucleotide primer sequence, provided that the primer sequence has sufficient complementarity with the sequence of the desired template strand to functionally provide a template-primer complex for the synthesis of the extension product.

Polymerase chain reaction (PCR) has been described in U.S. Pat. Nos. 4,683,195, 4,800,195, and 4,965,188, the entire disclosures of which are incorporated by reference herein.

An "siRNA" refers to a molecule involved in the RNA interference process for a sequence-specific post-transcriptional gene silencing or gene knockdown by providing small interfering RNAs (siRNAs) that has homology with the sequence of the targeted gene. Small interfering RNAs (siRNAs) can be synthesized in vitro or generated by ribonuclease III cleavage from longer dsRNA and are the mediators of sequence-specific mRNA degradation. Preferably, the siRNA of the invention are chemically synthesized using appropriately protected ribonucleoside phosphoramidites and a conventional DNA/RNA synthesizer. The siRNA can be synthesized as two separate, complementary RNA molecules, or as a single RNA molecule with two complementary regions. Commercial suppliers of synthetic RNA molecules or synthesis reagents include Applied Biosystems (Foster City, Calif., USA), Proligo (Hamburg, Germany), Dharmacon Research (Lafayette, Colo., USA), Pierce Chemical (part of Perbio Science, Rockford, Ill., USA), Glen Research (Sterling, Va., USA), ChemGenes (Ashland, Mass., USA) and Cruachem (Glasgow, UK). Specific siRNA constructs for inhibiting elevated mRNA levels associated with pancreatic cancer may be between 15-35 nucleotides in length, and more typically about 21 nucleotides in length.

The term "vector" relates to a single or double stranded circular nucleic acid molecule that can be infected, transfected or transformed into cells and replicate independently or within the host cell genome. A circular double stranded nucleic acid molecule can be cut and thereby linearized upon treatment with restriction enzymes. An assortment of vectors, restriction enzymes, and the knowledge of the nucleotide sequences that are targeted by restriction enzymes are readily available to those skilled in the art, and include any replicon, such as a plasmid, cosmid, bacmid, phage or virus, to which another genetic sequence or element (either DNA or RNA) may be attached so as to bring about the replication of the attached sequence or element. A nucleic acid molecule of the invention can be inserted into a vector by cutting the vector with restriction enzymes and ligating the two pieces together.

Many techniques are available to those skilled in the art to facilitate transformation, transfection, or transduction of the expression construct into a prokaryotic or eukaryotic organism. The terms "transformation", "transfection", and "transduction" refer to methods of inserting a nucleic acid and/or expression construct into a cell or host organism. These methods involve a variety of techniques, such as treating the cells with high concentrations of salt, an electric field, or detergent, to render the host cell outer membrane or wall permeable to nucleic acid molecules of interest, microinjection, peptide-tethering, PEG-fusion, and the like.

The term "promoter element" describes a nucleotide sequence that is incorporated into a vector that, once inside an appropriate cell, can facilitate transcription factor and/or polymerase binding and subsequent transcription of portions of the vector DNA into mRNA. In one embodiment, the promoter element of the present invention precedes the 5' end of the pancreatic cancer specific marker nucleic acid molecule(s) such that the latter is transcribed into mRNA. Host cell machinery then translates mRNA into a polypeptide.

Those skilled in the art will recognize that a nucleic acid vector can contain nucleic acid elements other than the promoter element and the pancreatic cancer specific marker gene nucleic acid molecule(s). These other nucleic acid elements include, but are not limited to, origins of replication, ribosomal binding sites, nucleic acid sequences encoding drug resistance enzymes or amino acid metabolic enzymes, and nucleic acid sequences encoding secretion signals, localization signals, or signals useful for polypeptide purification.

A "replicon" is any genetic element, for example, a plasmid, cosmid, bacmid, plastid, phage or virus that is capable of replication largely under its own control. A replicon may be either RNA or DNA and may be single or double stranded.

An "expression operon" refers to a nucleic acid segment that may possess transcriptional and translational control sequences, such as promoters, enhancers, translational start signals (e.g., ATG or AUG codons), polyadenylation signals, terminators, and the like, and which facilitate the expression of a polypeptide coding sequence in a host cell or organism.

As used herein, the terms "reporter," "reporter system", "reporter gene," or "reporter gene product" shall mean an operative genetic system in which a nucleic acid comprises a gene that encodes a product that when expressed produces a reporter signal that is a readily measurable, e.g., by biological assay, immunoassay, radio immunoassay, or by colorimetric, fluorogenic, chemiluminescent or other methods. The nucleic acid may be either RNA or DNA, linear or circular, single or double stranded, antisense or sense polarity, and is operatively linked to the necessary control elements for the expression of the reporter gene product. The required control elements will vary according to the nature of the reporter system and whether the reporter gene is in the form of DNA or RNA, but may include, but not be limited to, such elements as promoters, enhancers, translational control sequences, poly A addition signals, transcriptional termination signals and the like.

The introduced nucleic acid may or may not be integrated (covalently linked) into nucleic acid of the recipient cell or organism. In bacterial, yeast, plant and mammalian cells, for example, the introduced nucleic acid may be maintained as an episomal element or independent replicon such as a plasmid. Alternatively, the introduced nucleic acid may become integrated into the nucleic acid of the recipient cell or organism and be stably maintained in that cell or organism and further passed on or inherited to progeny cells or organisms of the recipient cell or organism. Finally, the introduced nucleic acid may exist in the recipient cell or host organism only transiently.

The term "selectable marker gene" refers to a gene that when expressed confers a selectable phenotype, such as antibiotic resistance, on a transformed cell.

The term "operably linked" means that the regulatory sequences necessary for expression of the coding sequence are placed in the DNA molecule in the appropriate positions relative to the coding sequence so as to effect expression of the coding sequence. This same definition is sometimes applied to the arrangement of transcription units and other transcription control elements (e.g. enhancers) in an expression vector.

The terms "recombinant organism," or "transgenic organism" refer to organisms which have a new combination of genes or nucleic acid molecules. A new combination of genes or nucleic acid molecules can be introduced into an organism using a wide array of nucleic acid manipulation techniques available to those skilled in the art. The term "organism" relates to any living being comprised of a least one cell. An organism can be as simple as one eukaryotic cell or as complex as a mammal. Therefore, the phrase "a recombinant organism" encompasses a recombinant cell, as well as eukaryotic and prokaryotic organism.

The term "isolated protein" or "isolated and purified protein" is sometimes used herein. This term refers primarily to a protein produced by expression of an isolated genetic signature nucleic acid or biomarker molecule of the invention. Alternatively, this term may refer to a protein that has been sufficiently separated from other proteins with which it would naturally be associated, so as to exist in "substantially pure" form. "Isolated" is not meant to exclude artificial or synthetic mixtures with other compounds or materials, or the presence of impurities that do not interfere with the fundamental activity and that may be present, for example, due to incomplete purification, addition of stabilizers, or compounding into, for example, immunogenic preparations or pharmaceutically acceptable preparations.

A "specific binding pair" comprises a specific binding member (sbm) and a binding partner (bp) which have a particular specificity for each other and which in normal conditions bind to each other in preference to other molecules. Examples of specific binding pairs are antigens and antibodies, ligands and receptors and complementary nucleotide sequences. The skilled person is aware of many other examples. Further, the term "specific binding pair" is also applicable where either or both of the specific binding member and the binding partner comprise a part of a large molecule. In embodiments in which the specific binding pair comprises nucleic acid sequences, they will be of a length to hybridize to each other under conditions of the assay, preferably greater than 10 nucleotides long, more preferably greater than 15 or 20 nucleotides long.

"Sample" or "patient sample" or "biological sample" generally refers to a sample which may be tested for a particular molecule or combination of molecules, preferably a combination of the biomarker or genetic signature marker molecules, such as a combination of the markers shown in the Tables below. Samples may include but are not limited to cells, cyst fluids, body fluids, including blood, serum, plasma, urine, saliva, tears, pleural fluid and the like.

The terms "agent" and "test compound" are used interchangeably herein and denote a chemical compound, a mixture of chemical compounds, a biological macromolecule, or an extract made from biological materials such as bacteria, plants, fungi, or animal (particularly mammalian) cells or tissues. Biological macromolecules include siRNA, shRNA, antisense oligonucleotides, small molecules, antibodies, peptides, peptide/DNA complexes, and any nucleic acid based molecule, for example an oligo, which exhibits the capacity to modulate the activity of the genetic signature nucleic acids described herein or their encoded proteins. Agents are evaluated for potential biological activity by inclusion in screening assays described herein below.

The term "modulate" as used herein refers increasing or decreasing. For example, the term modulate refers to the ability of a compound or test agent to either interfere with, or augment signaling or activity of a gene or protein of the present invention.

Methods of Using the Biomarkers and Genetic Signatures of the Invention

Genetic signature or biomarker encoding nucleic acids, including but not limited to those listed in the Tables hereinbelow may be used for a variety of purposes in accordance with the present invention. The genetic signature associated with an increased risk of pancreatic cancer (e.g., the plurality of nucleic acids contained therein) containing DNA, RNA, or fragments thereof may be used as probes to detect the presence of and/or expression of these specific markers in a biological sample. Methods in which such marker nucleic acids may be utilized as probes for such assays include, but are not limited to: (1) in situ hybridization; (2) Southern hybridization (3) northern hybridization; and (4) assorted amplification reactions such as polymerase chain reactions (PCR).

Further, assays for detecting the genetic signature may be conducted on any type of biological sample, but is most preferably performed on cyst fluid. From the foregoing discussion, it can be seen that genetic signature containing nucleic acids, vectors expressing the same, genetic signature encoded proteins and anti-genetic signature encoded protein specific antibodies of the invention can be used to detect the signature in body tissue, cells, or fluid, and alter genetic signature containing marker protein expression for purposes of assessing the genetic and protein interactions involved in pancreatic cancer.

In certain embodiments for screening for genetic signature containing nucleic acid(s), the sample will initially be amplified, e.g. using PCR, to increase the amount of the template as compared to other sequences present in the sample. This allows the target sequences to be detected with a high degree of sensitivity if they are present in the sample. This initial step may be avoided by using highly sensitive array techniques that are becoming increasingly important in the art.

Alternatively, alternative detection technologies will be employed which detect the pancreatic cancer biomarker proteins directly. Such methods include geLC/MS/MS proteomics analysis. This approach provides a full panel of the protein biomarkers present in cyst fluid and allows the clinician to predict outcomes based on the panel of biomarkers present in a sample.

Thus, any of the aforementioned techniques may be used to detect or quantify genetic signature expression and or protein expression levels and accordingly, diagnose patient susceptibility for developing pancreatic cancer.

Kits and Articles of Manufacture

Any of the aforementioned products can be incorporated into a kit which may contain genetic signature polynucleotides or one or more such markers immobilized on a Gene Chip, an oligonucleotide, a polypeptide, a peptide, an antibody, a label, marker, or reporter, a pharmaceutically acceptable carrier, a physiologically acceptable carrier, instructions for use, a container, a vessel for administration, an assay substrate, or any combination thereof.

Methods of Using the Genetic Signature or Biomarker Proteins for Development of Therapeutic Agents Since the genetic signature identified herein and the proteins encoded thereby has been associated with the etiology of pancreatic cancer, methods for identifying agents that modulate the activity of the genes and their encoded products should result in the generation of efficacious therapeutic agents for the treatment of a cancer, particularly pancreatic cancer.

The nucleic acids comprising the signature contain regions which provide suitable targets for the rational design of therapeutic agents which modulate their activity. Small peptide molecules corresponding to these regions may be used to advantage in the design of therapeutic agents which effectively modulate the activity of the encoded proteins. Molecular modeling should facilitate the identification of specific organic molecules with capacity to bind to the active site of the proteins encoded by the genetic signature nucleic acids based on conformation or key amino acid residues required for function. A combinatorial chemistry approach will be used to identify molecules with greatest activity and then iterations of these molecules will be developed for further cycles of screening. In certain embodiments, candidate agents can be screening from large libraries of synthetic or natural compounds. Such compound libraries are commercially available from a number of companies including but not limited to Maybridge Chemical Co., (Trevillet, Cornwall, UK), Comgenex (Princeton, N.J.), Microsour (New Milford, Conn.) Aldrich (Milwaukee, Wis.) Akos Consulting and Solutions GmbH (Basel, Switzerland), Ambinter (Paris, France), Asinex (Moscow, Russia) Aurora (Graz, Austria), BioFocus DPI (Switzerland), Bionet (Camelford, UK), Chembridge (San Diego, Calif.), Chem Div (San Diego, Calif.). The skilled person is aware of other sources and can readily purchase the same. Once therapeutically efficacious compounds are identified in the screening assays described herein, they can be formulated in to pharmaceutical compositions and utilized for the treatment of pancreatic cancer.

The polypeptides or fragments employed in drug screening assays may either be free in solution, affixed to a solid support or within a cell. One method of drug screening utilizes eukaryotic or prokaryotic host cells which are stably transformed with recombinant polynucleotides expressing the biomarker polypeptide or fragment, preferably in competitive binding assays. Such cells, either in viable or fixed form, can be used for standard binding assays. One may determine, for example, formation of complexes between the polypeptide or fragment and the agent being tested, or examine the degree to which the formation of a complex between the polypeptide or fragment and a known substrate is interfered with by the agent being tested.

Another technique for drug screening provides high throughput screening for compounds having suitable binding affinity for the encoded polypeptides and is described in detail in Geysen, PCT published application WO 84/03564, published on Sep. 13, 1984. Briefly stated, large numbers of different, small peptide test compounds, such as those described above, are synthesized on a solid substrate, such as plastic pins or some other surface. The peptide test compounds are reacted with the target polypeptide and washed. Bound polypeptide is then detected by methods well known in the art.

A further technique for drug screening involves the use of host eukaryotic cell lines or cells (such as described above) which have a nonfunctional or altered pancreatic cancer associated gene. These host cell lines or cells are defective at the polypeptide level. The host cell lines or cells are grown in the presence of drug compound. The effect on cellular morphology and/or proliferation of the host cells is measured to determine if the compound is capable of regulating the same in the defective cells. Host cells contemplated for use in the present invention include but are not limited to bacterial cells, fungal cells, insect cells, mammalian cells, particularly pancreatic cells. The genetic signature encoding DNA molecules may be introduced singly into such host cells or in combination to assess the phenotype of cells conferred by such expression. Methods for introducing DNA molecules are also well known to those of ordinary skill in the art. Such methods are set forth in Ausubel et al. eds., Current Protocols in Molecular Biology, John Wiley & Sons, NY, N.Y. 1995, the disclosure of which is incorporated by reference herein.

Pancreatic cells and pancreatic cell lines suitable for studying the effects of genetic signature expression on cellular morphology and signaling methods of use thereof for drug discovery are provided. Such cells and cell lines will be transfected with genetic signature encoding nucleic acids described herein and the effects on pancreatic cell functions and/or cyst formation can be determined. Such cells and cell lines can also be contacted with the siRNA molecules provided herein to assess the effects thereof on malignant transformation. The siRNA molecules will be tested alone and in combination of 2, 3, 4, and 5 siRNAs to identify the most efficacious combination for down regulating target nucleic acids.

A wide variety of expression vectors are available that can be modified to express the novel DNA or RNA sequences of this invention. The specific vectors exemplified herein are merely illustrative, and are not intended to limit the scope of the invention. Expression methods are described by Sambrook et al. Molecular Cloning: A Laboratory Manual or Current Protocols in Molecular Biology 16.3-17.44 (1989). Expression methods in *Saccharomyces* are also described in Current Protocols in Molecular Biology (1989).

Suitable vectors for use in practicing the invention include prokaryotic vectors such as the pNH vectors (Stratagene Inc., 11099 N. Torrey Pines Rd., La Jolla, Calif. 92037), pET vectors (Novogen Inc., 565 Science Dr., Madison, Wis. 53711) and the pGEX vectors (Pharmacia LKB Biotechnology Inc., Piscataway, N.J. 08854). Examples of eukaryotic vectors useful in practicing the present invention include the vectors pRc/CMV, pRc/RSV, and pREP (Invitrogen, 11588 Sorrento Valley Rd., San Diego, Calif. 92121); pcDNA3.1/ V5&His (Invitrogen); baculovirus vectors such as pVL1392, pVL1393, or pAC360 (Invitrogen); and yeast vectors such as YRP17, YIP5, and YEP24 (New England Biolabs, Beverly, Mass.), as well as pRS403 and pRS413 Stratagene Inc.); Picchia vectors such as pHIL-D1 (Phillips Petroleum Co., Bartlesville, Okla. 74004); retroviral vectors such as PLNCX and pLPCX (Clontech); and adenoviral and adeno-associated viral vectors.

Promoters for use in expression vectors of this invention include promoters that are operable in prokaryotic or eukaryotic cells. Promoters that are operable in prokaryotic cells include lactose (lac) control elements, bacteriophage lambda (pL) control elements, arabinose control elements, tryptophan (trp) control elements, bacteriophage T7 control elements, and hybrids thereof. Promoters that are operable in eukaryotic cells include Epstein Barr virus promoters, adenovirus promoters, SV40 promoters, Rous Sarcoma Virus promoters, cytomegalovirus (CMV) promoters, baculovirus promoters such as AcMNPV polyhedrin promoter, Picchia promoters such as the alcohol oxidase promoter, and *Saccharomyces* promoters such as the gal4 inducible promoter and the PGK constitutive promoter, as well as neuronal-specific platelet-derived growth factor promoter (PDGF).

In addition, a vector of this invention may contain any one of a number of various markers facilitating the selection of a transformed host cell. Such markers include genes associated with temperature sensitivity, drug resistance, or enzymes associated with phenotypic characteristics of the host organisms.

Host cells expressing the genetic signature of the present invention or functional fragments thereof provide a system in which to screen potential compounds or agents for the ability to modulate the development of pancreatic cancer Another approach entails the use of phage display libraries engineered to express fragment of the polypeptides encoded by the genetic signature containing nucleic acids on the phage surface. Such libraries are then contacted with a combinatorial chemical library under conditions wherein binding affinity between the expressed peptide and the components of the chemical library may be detected. U.S. Pat. Nos. 6,057,098 and 5,965,456 provide methods and apparatus for performing such assays.

The goal of rational drug design is to produce structural analogs of biologically active polypeptides of interest or of small molecules with which they interact (e.g., agonists, antagonists, inhibitors) in order to fashion drugs which are, for example, more active or stable forms of the polypeptide, or which, e.g., enhance or interfere with the function of a polypeptide in vivo. See, e.g., Hodgson, (1991) Bio/Technology 9:19-21. In one approach, discussed above, the three-dimensional structure of a protein of interest or, for example, of the protein-substrate complex, is solved by x-ray crystallography, by nuclear magnetic resonance, by computer modeling or most typically, by a combination of approaches. Less often, useful information regarding the structure of a polypeptide may be gained by modeling based on the structure of homologous proteins. An example of rational drug design is the development of HIV protease inhibitors (Erickson et al., (1990) Science 249:527-533). In addition, peptides may be analyzed by an alanine scan (Wells, (1991) Meth. Enzym. 202:390-411). In this technique, an amino acid residue is replaced by Ala, and its effect on the peptide's activity is determined. Each of the amino acid residues of the peptide is analyzed in this manner to determine the important regions of the peptide.

It is also possible to isolate a target-specific antibody, selected by a functional assay, and then to solve its crystal structure. In principle, this approach yields a pharmacophore upon which subsequent drug design can be based.

One can bypass protein crystallography altogether by generating anti-idiotypic antibodies (anti-ids) to a functional, pharmacologically active antibody. As a mirror image of a mirror image, the binding site of the anti-ids would be expected to be an analog of the original molecule. The anti-id could then be used to identify and isolate peptides from banks of chemically or biologically produced banks of peptides. Selected peptides would then act as the pharmacophore.

Thus, one may design drugs which have, e.g., improved polypeptide activity or stability or which act as inhibitors, agonists, antagonists, etc. of polypeptide activity. By virtue of the availability of the genetic signature containing nucleic acid sequences described herein, sufficient amounts of the encoded polypeptide may be made available to perform such analytical studies as x-ray crystallography. In addition, the knowledge of the protein sequence provided herein will guide those employing computer modeling techniques in place of, or in addition to x-ray crystallography.

In another embodiment, the availability of genetic signature containing nucleic acids enables the production of strains of laboratory mice carrying the signature(s) of the invention. Transgenic mice expressing the genetic signature of the invention provide a model system in which to examine the role of the protein(s) encoded by the signature containing nucleic acid in the development and progression towards pancreatic cancer. Methods of introducing transgenes in laboratory mice are known to those of skill in the art. Three common methods include: (1) integration of retroviral vectors encoding the foreign gene of interest into an early embryo; (2) injection of DNA into the pronucleus of a newly fertilized egg; and (3) the incorporation of genetically manipulated embryonic stem cells into an early embryo. Production of the transgenic mice described above will facilitate the molecular elucidation of the role that a target protein plays in various cellular metabolic processes. Such mice provide an in vivo screening tool to study putative therapeutic drugs in a whole animal model and are encompassed by the present invention.

The term "animal" is used herein to include all vertebrate animals, except humans. It also includes an individual animal in all stages of development, including embryonic and fetal stages. A "transgenic animal" is any animal containing one or more cells bearing genetic information altered or received, directly or indirectly, by deliberate genetic manipulation at the subcellular level, such as by targeted recombination or microinjection or infection with recombinant virus. The term "transgenic animal" is not meant to encompass classical cross-breeding or in vitro fertilization, but rather is meant to encompass animals in which one or more cells are altered by or receive a recombinant DNA molecule. This molecule may be specifically targeted to a defined genetic locus, be randomly integrated within a chromosome, or it may be extra-chromosomally replicating DNA. The term "germ cell line transgenic animal" refers to a transgenic animal in which the genetic alteration or genetic information was introduced into a germ line cell, thereby conferring the ability to transfer the genetic information to offspring. If such offspring, in fact, possess some or all of that alteration or genetic information, then they, too, are transgenic animals.

The alteration of genetic information may be foreign to the species of animal to which the recipient belongs, or foreign only to the particular individual recipient, or may be genetic information already possessed by the recipient. In the last case, the altered or introduced gene may be expressed differently than the native gene. Such altered or foreign genetic information would encompass the introduction of genetic signature containing nucleotide sequences.

The DNA used for altering a target gene may be obtained by a wide variety of techniques that include, but are not limited to, isolation from genomic sources, preparation of cDNAs from isolated mRNA templates, direct synthesis, or a combination thereof.

A preferred type of target cell for transgene introduction is the embryonal stem cell (ES). ES cells may be obtained from pre-implantation embryos cultured in vitro (Evans et al., (1981) Nature 292:154-156; Bradley et al., (1984) Nature 309:255-258; Gossler et al., (1986) Proc. Natl. Acad. Sci. 83:9065-9069). Transgenes can be efficiently introduced into the ES cells by standard techniques such as DNA transfection or by retrovirus-mediated transduction. The resultant transformed ES cells can thereafter be combined with blastocysts from a non-human animal. The introduced ES cells thereafter colonize the embryo and contribute to the germ line of the resulting chimeric animal.

One approach to the problem of determining the contributions of individual genes and their expression products is to use genetic signature associated genes as insertional cassettes to selectively inactivate a wild-type gene in totipotent ES cells (such as those described above) and then generate transgenic mice. The use of gene-targeted ES cells in the generation of gene-targeted transgenic mice was described, and is reviewed elsewhere (Frohman et al., (1989) Cell 56:145-147; Bradley et al., (1992) Bio/Technology 10:534-539).

Techniques are available to inactivate or alter any genetic region to a mutation desired by using targeted homologous recombination to insert specific changes into chromosomal alleles. However, in comparison with homologous extra-chromosomal recombination, which occurs at a frequency approaching 100%, homologous plasmid-chromosome recombination was originally reported to only be detected at frequencies between $10^{-6}$ and $10^{-3}$. Non-homologous plasmid-chromosome interactions are more frequent occurring at levels $10^5$-fold to $10^2$ fold greater than comparable homologous insertion.

To overcome this low proportion of targeted recombination in murine ES cells, various strategies have been developed to detect or select rare homologous recombinants. One approach for detecting homologous alteration events uses the polymerase chain reaction (PCR) to screen pools of transformant cells for homologous insertion, followed by screening of individual clones. Alternatively, a positive genetic selection approach has been developed in which a marker gene is constructed which will only be active if homologous insertion occurs, allowing these recombinants to be selected directly. One of the most powerful approaches developed for selecting homologous recombinants is the positive-negative selection (PNS) method developed for genes for which no direct selection of the alteration exists. The PNS method is more efficient for targeting genes which are not expressed at high levels because the marker gene has its own promoter. Non-homologous recombinants are selected against by using the Herpes Simplex virus thymidine kinase (HSV-TK) gene and selecting against its nonhomologous insertion with effective herpes drugs such as gancyclovir (GANC) or (1-(2-deoxy-2-fluoro-B-D arabinofluranosyl)-5-iodou-racil, (FIAU). By this counter selection, the number of homologous recombinants in the surviving transformants can be increased. Utilizing genetic signature containing nucleic acid as a targeted insertional cassette provides means to detect a successful insertion as visualized, for example, by acquisition of immunoreactivity to an antibody immunologically specific for the polypeptide encoded genetic signature nucleic acid(s) and, therefore, facilitates screening/selection of ES cells with the desired genotype.

As used herein, a knock-in animal is one in which the endogenous murine gene, for example, has been replaced with human genetic signature-associated gene(s) of the invention. Such knock-in animals provide an ideal model system for studying the development of pancreatic cancer.

As used herein, the expression of a genetic signature containing nucleic acid, fragment thereof, or genetic signature fusion protein can be targeted in a "tissue specific manner" or "cell type specific manner" using a vector in which nucleic acid sequences encoding all or a portion of genetic signature-associated protein are operably linked to regulatory sequences (e.g., promoters and/or enhancers) that direct expression of the encoded protein in a particular tissue or cell type. Such regulatory elements may be used to advantage for both in vitro and in vivo applications. Promoters for directing tissue specific expression of proteins are well known in the art and described herein.

Methods of use for the transgenic mice of the invention are also provided herein. Transgenic mice into which a nucleic acid containing the genetic signature or its encoded protein(s) have been introduced are useful, for example, to develop screening methods to screen therapeutic agents to identify those capable of modulating the development of pancreatic cancer.

Pharmaceuticals and Peptide Therapies

The elucidation of the role played by the gene products described herein in pancreatic cancer progression facilitates the development of pharmaceutical compositions useful for treatment and diagnosis of pancreatic cancer. These compositions may comprise, in addition to one of the above substances, a pharmaceutically acceptable excipient, carrier, buffer, stabilizer or other materials well known to those skilled in the art. Such materials should be non-toxic and should not interfere with the efficacy of the active ingredient.

Whether it is a polypeptide, antibody, peptide, nucleic acid molecule, small molecule or other pharmaceutically useful compound according to the present invention that is to be given to an individual, administration is preferably in a "prophylactically effective amount" or a "therapeutically effective amount" (as the case may be, although prophylaxis may be considered therapy), this being sufficient to show benefit to the individual.

As it is presently understood, RNA interference involves a multi-step process. Double stranded RNAs are cleaved by the endonuclease Dicer to generate nucleotide fragments (siRNA). The siRNA duplex is resolved into 2 single stranded RNAs, one strand being incorporated into a protein-containing complex where it functions as guide RNA to direct cleavage of the target RNA (Schwarz et al, Mol. Cell. 10:537 548 (2002), Zamore et al, Cell 101:25 33 (2000)), thus silencing a specific genetic message (see also Zeng et al, Proc. Natl. Acad. Sci. 100:9779 (2003)).

Pharmaceutical compositions that are useful in the methods of the invention may be administered systemically in parenteral, oral solid and liquid formulations, ophthalmic, suppository, aerosol, topical or other similar formulations. These pharmaceutical compositions may contain pharmaceutically-acceptable carriers and other ingredients known to enhance and facilitate drug administration. Thus such compositions may optionally contain other components, such as adjuvants, e.g., aqueous suspensions of aluminum and magnesium hydroxides, and/or other pharmaceutically acceptable carriers, such as saline. Other possible formulations, such as nanoparticles, liposomes, resealed erythrocytes, and immunologically based systems may also be used to administer the appropriate agent to a patient according to the methods of the invention. The use of nanoparticles to deliver agents, as well as cell membrane permeable peptide carriers that can be used are described in Crombez et al., Biochemical Society Transactions v35:p44 (2007).

In order to treat an individual having pancreatic cancer, to alleviate a sign or symptom of the disease, the pharmaceutical agents of the invention should be administered in an effective dose. The total treatment dose can be administered to a subject as a single dose or can be administered using a fractionated treatment protocol, in which multiple doses are administered over a more prolonged period of time, for example, over the period of a day to allow administration of a daily dosage or over a longer period of time to administer a dose over a desired period of time. One skilled in the art would know that the amount of agent required to obtain an effective dose in a subject depends on many factors, including the age, weight and general health of the subject, as well as the route of administration and the number of treatments to be administered. In view of these factors, the skilled artisan would adjust the particular dose so as to obtain an effective dose for treating an individual having pancreatic cancer.

In an individual suffering from pancreatic cancer, in particular a more severe form of the disease, administration of agent can be particularly useful when administered in combination, for example, with a conventional agent for treating such a disease. The skilled artisan would administer the agent alone or in combination and would monitor the effectiveness of such treatment using routine methods such as sonogram, radiologic, immunologic or, where indicated, histopathologic methods. Other conventional agents for the treatment of pancreatic cancer include anti cancer agents, such as gemcitabine and erlotinib. Administration of the pharmaceutical preparation is preferably in an "effective amount" this being sufficient to show benefit to the individual. This amount prevents, alleviates, abates, or otherwise reduces the severity of pancreatic cancer symptoms in a patient.

The pharmaceutical preparation is formulated in dosage unit form for ease of administration and uniformity of dosage. Dosage unit form, as used herein, refers to a physically discrete unit of the pharmaceutical preparation appropriate for the patient undergoing treatment. Each dosage should contain a quantity of active ingredient calculated to produce the desired effect in association with the selected pharmaceutical carrier. Procedures for determining the appropriate dosage unit are well known to those skilled in the art.

Dosage units may be proportionately increased or decreased based on the weight of the patient. Appropriate concentrations for alleviation of a particular pathological condition may be determined by dosage concentration curve calculations, as known in the art.

The Examples below are provided to illustrate certain embodiments of the invention. They are not intended to limit the invention in any way.

EXAMPLE I

Proteomic Analysis of Pancreatic Cancer Fluids

The following materials and methods are provided to facilitate the practice of the present invention.

Sample Acquisition. Aliquots of cyst fluid that were used for this project were obtained from materials that were aspirated for clinical purposes. The study was approved by the Institutional Review Board of the Fox Chase Cancer Center. EUS-FNA (14) was performed under conscious sedation using a linear echoendoscope. When a lesion was identified, EUS-FNA was performed with a 22 or 19-gauge needle through either a transduodenal or transgastric approach, depending on the location of the lesion within the pancreas. The highest priority was given to procuring a volume of fluid that was adequate to perform the necessary clinically indicated diagnostic assays (e.g., cytology, CEA in ng/mL, Mayo Medical Laboratories, code #84074), amylase (in units/L, Mayo Medical Laboratories, code #5079). As little as 40 µL of cyst fluids per patient were allocated for the proteomic study. For the purpose of this study, cyst fluid cytology findings were grouped into the following categories: A—Benign: No evidence of benign mucinous epithelium, atypical cells or carcinoma; B—Benign mucinous epithelium; C—Atypical/suspicious cytology; D—Malignant.

Proteomics Analysis. Standard Operating Procedures were established and followed for all steps of cyst fluid collection and analysis. The cyst fluid was diluted with three volumes of PBS, mixed, and centrifuged for 10 minutes at 13,000×g at 4° C. to remove cells and any insoluble materials, snap frozen in liquid nitrogen in aliquots and banked at −80° C. To remove small peptides bound to larger proteins, the cyst fluid was treated with three volumes of 0.1M glycine pH 2.3 and acetonitrile was added to 25% v/v final concentration. The solution was filtered by ultrafiltration (pre-washed Amicon YM-30 Centricon #4208) at 4000×g at 4° C. for about one hour to reach minimum retention volume designed for the unit. The retained proteins above the filter were solubilized with 200 μL of 0.2% SDS solution and transferred to a 1.5 mL microcentrifuge tube. Three volumes of cold acetone were added to precipitate the proteins overnight at −20° C. and the suspension was then centrifuged at 21,000×g for 40 min. The pellet was washed once with 80% cold acetone, centrifuged, and air dried, then resolubilized in 2D PAGE sample buffer (7 M urea, 2 M thiourea, 4% (w/v) CHAPS). Protein concentration was determined as previously described (15).

Protein (15 μg) was reduced with dithiothreitol and alkylated by iodoacetamide at 25° C. for 1 hr (15) and then resolved in a pre-cast Novex 4-12% gradient PAGE with 3 mm wide wells (Invitrogen™, CA, USA). Electrophoresis was performed in MOPS buffer at 150V at room temperature for about 20 min until the tracking dye was 1.5 cm from the top of the gel. The gel cassette was opened in a laminar flow hood. Each sample lane, two per gel, was cut into 11 slices from the well to about 2 mm beyond the dye front. Each gel slice was again subjected to reduction and alkylation. Porcine trypsin (Sigma proteomic grade #T6567) was added as 63 ng in 7 μL 25 mM ammonium bicarbonate and incubated for 30 min. Unabsorbed trypsin of about 2 μL was removed and 20 μL of 25 mM ammonium bicarbonate was added and incubated at 37° C. for about 16 hours. 10 μL of the peptide solution was mixed with 2.5 μL of 25% acetonitrile 1% formic acid, and 2 μL was injected into the LC/MS/MS system for protein identification. A LC/MS/MS system consisted of an Applied Biosystems QSTAR XL hybrid quadruple TOF mass spectrometer supported by an Agilent nanoLC system. For 15 μg gel loading, 10% of the digest of each gel slice was auto-injected onto a trap column (Agilent Zorbax 300SB-C18, 5 μm, 5×0.3 mm), washed, and eluted at 0.3 μL/min through an analytical column (Agilent Zorbax 300SB-C18, 3.5 μm, 150×0.1 mm) at room temperature. The elution gradient was in 0.2% formic acid with linear segments of 4.5%, 4.5%, 28%, 54%, 90% acetonitrile at 0, 4, 8, 80, 85 min, respectively. An IDA protocol using MS periods of 2 s of TOF-MS and three cycles of 4 s of MS/MS each was used to obtain highly accurate spectra for protein identification for the three most intense peptide ions in each cycle. For discovery of more proteins and peptides in cyst fluids and to overcome the possibility of false-negatives due to under-sampling of co-eluting peptides, an exclusion list of the peptides in the first LC/MS/MS run of a cyst fluid was used to direct the second LC/MS/MS run to sequence new peptides. The two peak lists were combined for database searching for protein identification and for relative quantitation of the proteins by emPAI score (exponentially modified protein abundance index) without isotope labeling (16). The emPAI score, [10^(# observed peptides/# theoretical peptides)−1], is roughly proportional to the abundance of a protein in a complex mixture. Almost every protein identified in Tables 1-3 was abundant enough to be identified, and its relative abundance quantified for comparison, in the first LC/MS/MS run.

Results

Pancreatic cyst fluids were obtained by EUS from 20 patients for geLC/MS/MS proteomics analysis. The proteins of pancreatic cyst fluids can be subjected to proteolysis in some situations if the pancreatic proteases are inadvertently activated, and if inhibition by serum protease inhibitors is ineffective. To avoid this problem, proteins that were larger than 10,000 in molecular weight were analyzed and quantification performed at the level of tryptic peptides. For the analysis described herein, pancreatic cyst fluids appeared robust and stable, providing the same mass spectrometry information after multiple freeze-thaw cycles. The samples were unaffected by room temperature incubation (data not shown). However, cyst fluids are rich in small peptides bound to other carrier proteins in the sample. Our fractionation procedure removed these small peptides (data not shown), simplified the mass spectra obtained by geLC/MS/MS, and significantly increased the sensitivity of biomarker detection.

Clinical Information on the Cyst Fluids. Demography of the patients, dimensions of the cysts, and the results of traditional clinical tests performed on the cyst fluids are shown in Table 1. In Tables 1 to 4, because CEA measurements by clinical immunoassays are believed to be the strongest indicators of mucinous versus non-mucinous cysts in the absence of direct measurement of the mucins, the cysts are presented in the order of increasing CEA. Two samples without CEA values were located on the right side because high CEA values would be anticipated based on the histopathology findings.

All the patients were Caucasians. The various diagnostic assays, commercial amylase and CEA levels, were not obtained for all study patients. These absent values are represented by empty boxes in Table 1. For cysts 17, 14, 20, 5, and 21, subsequent surgical resection led to definitive histopathologic diagnosis as shown. Cyst 19B, diagnosed by histology after surgical resection as an IPMN adenoma, was the same patient as cyst 19A except the latter occurred five months before the surgical resection, providing a view of the biomarker transition.

The Pancreatic Cyst Fluid Proteome. Samples were purified and analyzed by geLC/MS/MS as described in Materials and Methods. The cyst fluids in this study vary in the amounts of plasma proteins versus pancreatic enzymes. About 137 proteins normally found in plasma were observed among 13 of the pancreatic cyst fluids. A partial list of these proteins is shown in Table 2. Hemoglobin, IgG, serum albumin, apolipoprotein A1 and AII, and serotransferrin were among the most abundant serum proteins when present. Hemoglobin was found in significant quantities only in five of the 20 cysts, suggesting that there was minimal contamination of blood from needle puncture during EUS-FNA collection of the cyst fluids. If red blood cells were present, they were successfully removed by centrifugation. Eight of the cyst fluids that contained the most plasma infiltration did not contain pancreatic enzymes. For example cysts 15 and 1 contained only plasma proteins (Table 2), no detectable pancreatic enzymes (Table 3), no mucins, no CEACAM, and no S100 homologs (Table 4). Seven of the cyst fluid samples were essentially free of proteins from blood. Most of these contained abundant pancreatic enzymes. The distribution of some of the 29 pancreatic enzymes among the cysts in this study is shown in Table 3. These enzymes included digestive enzymes and proteins important to pancreatic function. The latter included the pancreatic stone protein Lithostathine 1, the Regenerating islet-derived protein 3 alpha that has multiple functions, and Pancreatic secretory granule membrane major glycoprotein GP2. Amylase is not always observed in cysts that contained abundant levels of other pancreatic enzymes.

Data Analysis. Samples were purified and analyzed by geLC/MS/MS as described above. The mass spectrometry "wiff" data files were used to search the SwissProt protein database release 54.1 using MASCOT 2.2 (Matrix Sciences, London, U.K.), analyzing the MS/MS sequencing spectra of the +2 and +3 ions. Fixed modification of carbamidomethylcysteine, variable oxidation of methionine, and one trypsin miss were allowed for protein identification, but the latter two were disallowed for calculating the emPAI scores. Peptide mass tolerance was +/−150 ppm and fragment mass tolerance was 0.5 Da. False discovery rate was less than 3.5% for individual peptides as judged by hits at a decoy database with randomized sequences in each entry. Thus the confidence of correct protein identification is very high when three or more unique peptides with high quality sequencing spectra, and from the same position in the gel, are congruent in their identification of a protein in this project.

The presence of major protein classes of blood proteins, pancreatic enzymes, and keratins, in each sample, and the limited number of definitively histopathologically identified samples in this study, confound effective classification of the potential biomarkers by typical statistical approaches that include unsupervised hierarchical clustering (17) and principal component analysis (18). Low abundance proteins with an emPAI score average for the expressing samples of less than 0.01 were first removed, leaving 466 proteins identified with confidence. This emPAI score represents about one peptide sequence identified in a protein of about 250,000 molecular weight thus some of the lower score protein identifications were within the approximately 3% false positive identification rate for this data. Next, 34 keratins, 137 blood proteins, and 29 pancreatic enzymes, were filtered from the proteome of each cyst fluid sample. The remaining 295 proteins were sorted by the average emPAI score calculated from the samples expressing each protein. Among the most abundant ones in this list of pancreatic cyst fluid proteins were the homologs of three families of proteins previously proposed to be biomarkers of pancreatic cancer, namely mucins, CEACAM's (19), and S100's (20-22).

Proteomics Biomarkers. Several biomarkers, some of whose homologs are known to be elevated in pancreatic cancer, were identified in the cyst fluids (Table 4). Ten of the cyst fluids contained one or more mucin homologs, some of which have low amino acid sequence homology to each other. Cyst fluid from seven of the patients revealed the presence of CEACAM homologs by mass spectrometry detection. Five of the patients showed expression of S100 protein homologs in their cyst fluid. The relative abundances of CEACAM5 (CEA) determined by emPAI score were in rough agreement with the clinical assays performed on the samples shown in Table 1, bearing in mind the differences in CEA measurement procedures. More specifically, the emPAI score for CEACAM5 was determined as score per unit protein used in mass spectrometry while the clinical immunoassay CEA unit was concentration in ng per mL cyst fluid. In each case where the identification of a proteomic biomarker was at low abundance in a given cyst fluid, we ruled out the possibility of sample carry over by verifying that the same biomarker was not detected in the cyst fluid loaded onto the HPLC column in the preceding sample.

Discussion

Pancreatic cyst fluid aspired via EUS-FNA are used clinically to provide biomarkers that facilitate the diagnosis of the potential of pancreatic cancer in patients. The number of assays feasible for each patient is often limited by the quantity of cyst fluids available which is partly a function of the cyst size. For example, the volume of cyst fluids required to submit to either the clinical amylase assay or the clinical CEA assay used in this study is 0.5 mL. Moreover, cytologic diagnosis is facilitated using as large a cyst fluid sample as possible. The scarcity of cyst fluids in cysts smaller than one centimeter in diameter is one of the reasons why such small cysts are often not referred to EUS for evaluation. Thus, a new assay that provides for the measurement of mucins, amylase, and CEA in a minute volume of fluid, provides clinically relevant information in situations where the cyst fluid volumes are small. The proteome of pancreatic cyst fluids as elucidated by LC/MS/MS mass spectrometry proteomics provides comprehensive information on cancer biomarkers in pancreatic cyst fluids using a minimal volume of fluids. Interesting observations made on four classes of biomarkers are described below.

Amylase Biomarker. Although the measurement of amylase in blood has been a traditional biomarker of pancreatitis, the basis for using amylase measurements in pancreatic cyst fluid as an indicator of pancreatitis, non-mucinous cyst, or the absence of cancer has not been well studied. We show here that the pancreatic amylase activity in the cyst fluids is divided into two isozymes, alpha amylase 2B and pancreatic alpha amylase, encoded by two separate genes, AMY2B and AMY2A, respectively. The two isozymes have 98% sequence identity, but may differ in their regulation as shown in cysts 8, 10, 19B, and 14. Thus it may be pertinent to consider the levels of the two amylase isozymes individually. Amylase by itself is not always a good indicator of the presence of pancreatic enzymes as in the cases of 19B, cyst 3 and cyst 14 (Table 3). Although pancreatic lipases have been suggested as a substitute for amylase in the analysis of pancreatic cyst fluids, carboxypeptidases A1 and B may be equally effective as indicators of the presence of pancreatic enzymes in this set of samples. The simultaneous measurement of many pancreatic enzymes, made feasible by the use of mass spectrometry proteomics, may provide more complete information without the limitation of choosing one pancreatic enzyme as biomarker.

Abnormal expression of mucins and changes in their post-translational modification patterns have long been recognized as potential biomarkers of malignancy (3, 23). Table 4 shows that five soluble mucin homologs in cysts 2, 11, 9, and 19 can be distinguished and conveniently measured via LC/MS/MS proteomics and may assist in future classification of cysts. Soluble mucins were detected in these cases where the cytologists were unable to detect mucinous epithelial cells.

CEACAM Biomarkers. There are at least seven carcinoembryonic antigen homologs in humans (24, 25). The widely used CEA in clinical tests for various cancers (26) and in pancreatic cyst fluids is CEACAM5 (Table 1). For example, CEA levels of >400 ng/mL appear to be specific for mucin-producing cystic neoplasms (27). However, the CEA levels in these tumors is frequently lower, thus using a cutoff of 400 ng/mL may result in an unacceptably high "miss rate" for diagnosing these potentially malignant tumors (27). Alternatively, a level of 192 ng/mL has been cited as the "optimal" cutoff value (i.e., provides the best combined sensitivity and specificity for distinguishing mucinous from non-mucinous pancreatic cysts); however, this value results in an accuracy rate of only 79% (3). For example, cyst 14 had a CEA level of 582 ng/mL and amylase of 2853 U/L via clinical assays (Table 1) was found to be a MCA upon surgical histopathology. Accordingly, proteomics showed that there was downregulation of amylase in this enzyme cyst (Table 2) plus higher levels of the proteins of CEA homolog CEACAM6 and CEACAM7 than CEA (Table 4). Thus it appears that a combined high level of the CEACAM homologs are as important an indication as a high level of CEA by itself. As discussed below, the expression of S100A6 and S100A9 in this cyst are indicative of further progression for this neoplasm (Table 4). Cyst 3 with a clinical CEA assay of 63,830 had declined a Whipple procedure and thus had no pathology information. This high CEA value is consistent with its high mucin content and high CEACAM 5 and CEACAM 6 seen in proteomics (Table 4). However, the absence of S100 expression distinguish it from cysts 5, 14, and 21. Thus CEACAM homologs are markers that can assist in risk-stratifying pancreatic cysts.

S100 biomarkers. The S100 protein family includes small $Ca^{++}$ binding proteins that are soluble in 100% saturated ammonium sulfate solution and have long been recognized as biomarkers of brain cancer. A recent review provides references to the many cellular functions in which S100 homologs appear to participate (20). Although S100S8, S9 and S12 have been implicated as biomarkers of inflammation (28-30), no clinical pancreatitis was observed among the samples used in this study. Lu et al. observed that S100A9 was elevated in pancreatic carcinoma tissue compared with adjacent control tissue, and proposed that other S100 proteins may also serve as markers of pancreatic cancer (31). Recently, Ohuchida et al. extended this finding and showed that S100A6 and S100A11 are also elevated in pancreatic cancer tissue compared with controls and also in the ductal juices (21, 22). The confidence of identification of these S100 homologs A6, A8, A9, and A11 in the cyst fluids in our current study is very high. No peptides overlapped among the 15 peptides sequenced for the four S100 homologs. S100A8 was detected with 5 peptides sequenced and 54% amino acid sequence coverage while homolog S100A9 was distinguished using 6 peptides sequenced and 64% coverage. 43% sequence coverage was obtained for 3 peptides sequenced for S100A11. Only one peptide of excellent sequence quality and reproducibility was detected for S100A6.

Detectable significant levels of CEACAM homologs and S100 homologs in pancreatic cyst fluids, in addition to the presence of mucins and the loss of amylase, are useful biomarkers for the presence or potential of adenoma and carcinoma. This conclusion is supported by their presence in the five cysts, #17, 20, 5, 14, 21 that were confirmed by histopathology and cytopathology to be adenomas or carcinomas, but not at significant levels in cysts #13, 16, 18, 7, 19, 15, and 1. Cyst 5, an adenocarcinoma, is similar in cyst fluid proteome to non-mucinous cysts except for the presence of significant levels of CEACAM1, CEACAM5, and four S100 homologs. Cyst 21, a MCA, is similar in cyst fluid proteome to cyst 5 but with less of these proteins. For cyst 19B, a MCA, multiple potential biomarkers of mucins, CEACAM, and S100 are apparent. Five months earlier, when cyst 19B was aspired as cyst 19A, mass spectrometry had detected two CEACAMs and multiple mucins, consistent with the suggestion that CEA of greater than 192 ng/mL may indicate the presence of mucinous neoplasm (3). Thus S100 homologs are also useful markers of cyst progression.

Although the high mass accuracy and platform stability of the mass spectrometer used in this study facilitated biomarker discovery, once the protein names are known, another mass spectrometry method called Multiple Reaction Monitoring (MRM) can accurately quantify multiple biomarkers against internal standards at the same time with much higher sensitivity (32-35). Importantly, the quantitation of mucin homologs, CEACAM homologs, S100 homologs, amylase, and other marker proteins, can be performed at the same time using the same method, so their combination will provide valuable diagnostic and prognostic information to the clinician. The biomarkers described herein are obtainable from less than 40 µL of cyst fluids and detection of their presence facilitates earlier pancreatic cancer detection in cysts than heretofore previously possible.

EXAMPLE 2

Xenograft Model of Pancreatic Cancer and Pancreatic Cyst Fluid Secretion

The use of clinical samples for studying the biology of pancreatic cyst to cancer is difficult because of inability to obtain time course material in most instances, and because most invasive techniques of laboratory investigation cannot be used on patients. A mouse model, if valid and available, can accelerate pancreatic cancer research. For example, mouse stroma cells infiltrating the tumor and supports the tumor growth can be marked with Green Fluorescence Protein by using a GFP transgenic mouse as the host of the xenograft.

In the laboratory of Dr. Repasky, about 33% of pancreatic tumors engraftment resulted in successful tumor propagation for three passages for both adenocarcinomas and neuroendocrine tumors (38, 39). These xenograft tissues contain complex cell types from both cancer and stroma. The cancer cells form glands that hold secretions similar to what is seen in the parent tumors. We obtained three mice for us that harbored tumors soft to the touch. These mice are normally not used for preclinical drug treatment experiments. About 500 µL of fluids were collected from each of these xenograft and we analyzed them using the same protocol of GelC/MS/MS described in Example 1.

The high mass accuracy and sensitivity of our QSTAR XL mass spectrometer using LC/MS/MS produced numerous peptide sequences many of which easily distinguished human homologs of proteins from mouse homologs. This ability allowed us to interpret whether and how much mouse plasma and stroma are infiltrating the human tumors, and the origin of biomarker proteins detected in the xenograft fluids. Although these liquid cysts are often believed to result from necrosis, a process called cystic degeneration of tumors, in our mass spectrometry analysis of three independent xenograft fluids, we saw no evidence of general release of high abundance cellular proteins normally happening in necrosis. Similar to the pancreatic cyst fluids that did not contain pancreatic enzyme secretion, the xenograft fluids contained hundreds of plasma infiltrate proteins of mouse origin. However, human proteins were present, including abundant levels of pancreatic cyst fluid neoplasm biomarker proteins described in Example 1: mucin 1, mucins 5AC, mucin 5B, CEA, CEACAM 6, and S100A6 and S100A11. (Tables 3 and 4). Thus these "cancer cells" were secreting the same biomarkers as for the pancreatic cyst fluids from patients harboring cystadenoma, IPMN, and adenocarcinoma. Several other proteins in Table 5 below, not assigned as biomarkers in Example 1 are also seen in both cyst fluid and xenograft fluids, indicating that they can be functional biomarkers as well. Validating that our cyst fluid biomarkers can be secreted by pancreatic cancer xenograft was exciting, but cyst proteins conspicuously absent were CEACAM7, S100A8 and A9.

TABLE 5

Table 5. A partial list of proteins found in xenograft fluids from all three separate xenograft experiments. The numbers under each sample are EMPAI scores roughly proportional to the protein abundance in the sample. For comparison, serum albumin from mouse plasma infiltration or blood contamination has an average value of 12. The first 18 proteins, in bold, are also found among patient-derived pancreatic cyst fluids when cystadenoma, IPMN, or adenocarcinoma were indicated.

| Swiss-Prot Entry name | Title (Bold protein names are also found in pancreatic cyst fluids harboring cystadenoma, IPMN, or adenocarcinoma but not in benign cysts) | Mass (Da) | emPAI score Xenograft Sample 1 | emPAI score Xenograft Sample 2 | emPAI score Xenograft Sample 3 |
|---|---|---|---|---|---|
| ANXA2_HUMAN | Annexin A2 | 38808 | 6.61 | 9.04 | 3.38 |
| S10A6_HUMAN | Protein S100-A6 | 10230 | 1.71 | 0.94 | 0.94 |
| EZRI_HUMAN | Ezrin | 69484 | 1.42 | 1.83 | 0.52 |
| LG3BP_HUMAN | Galectin-3-binding protein | 66202 | 1.03 | 1.15 | 0.64 |
| S10AB_HUMAN | Protein S100-A11 | 11847 | 0.78 | 3.23 | 1.37 |
| GELS_HUMAN | Gelsolin | 86043 | 0.52 | 0.52 | 0.13 |
| MOES_HUMAN | Moesin | 67892 | 0.45 | 0.53 | 0.17 |
| ANXA1_HUMAN | Annexin A1 | 38918 | 0.44 | 0.58 | 0.74 |
| PIGR_HUMAN | Polymeric-immunoglobulin receptor | 84429 | 0.41 | 0.9 | 0.24 |
| NGAL_HUMAN | Neutrophil gelatinase-associated lipocalin | 22745 | 0.36 | 3.04 | 0.86 |
| ANXA3_HUMAN | Annexin A3 | 36524 | 0.34 | 0.34 | 0.48 |
| CEAM6_HUMAN | Carcinoembryonic antigen-related cell adhesion molecule 6 | 37499 | 0.33 | 0.46 | 0.21 |
| 1433S_HUMAN | 14-3-3 protein sigma | 27871 | 0.29 | 0.89 | 0.29 |
| MUC5A_HUMAN | Mucin-5AC | 135404 | 0.27 | 1.01 | 0.21 |
| CEAM5_HUMAN | Carcinoembryonic antigen-related cell adhesion molecule 5 | 77489 | 0.21 | 0.26 | 0.15 |
| MUC1_HUMAN | Mucin-1 | 122170 | 0.2 | 0.27 | 0.16 |
| MUC13_HUMAN | Mucin-13 | 55710 | 0.14 | 0.3 | 0.21 |
| MUC5B_HUMAN | Mucin-5B | 605803 | 0.08 | 0.16 | 0.21 |
| AGR2_HUMAN | Anterior gradient protein 2 | 20024 | 1.41 | 3.09 | 0.42 |
| ANXA5_HUMAN | Annexin A5 | 35971 | 1.22 | 1.7 | 0.82 |

Other biomarkers of interest include anterior gradient protein 2 which has been proposed as a marker of pancreatic cancer tissue because of its over-expression in most pancreatic cancers (40). Another interesting biomarkers is NGAL (Neutrophil gelatinase-associated lipocalin), a new early biomarker of acute kidney injury in rats. Its level in blood rises within two hours of renal injury. The protein is a member of the large lipocalin family of extracellular proteins which transports or binds small hydrophilic molecules, but when located inside a cell may become protease inhibitors. Its role in pancreatic cyst fluids is may be partly associated with inflammation.

Proteomics has resulted in the identification of biomarkers present in cysts, a better understanding of the basic biological features of cysts and their natural history, thereby providing a better understanding of the molecular profile within these cysts. Such information can be used to advantage to identify clinically relevant targets for early diagnosis and treatment of pancreatic cancer.

REFERENCES

1. Yeo, C. J., and Sarr, M. G. Cystic and pseudocystic diseases of the pancreas. Curr Probl Surg, 31: 165-243, 1994.
2. Shami, V. M., Sundaram, V., Stelow, E. B., Conaway, M., Moskaluk, C. A., White, G. E., Adams, R. B., Yeaton, P., and Kahaleh, M. The level of carcinoembryonic antigen and the presence of mucin as predictors of cystic pancreatic mucinous neoplasia. Pancreas, 34: 466-9, 2007.
3. Brugge, W. R., Lewandrowski, K., Lee-Lewandrowski, E., Centeno, B. A., Szydlo, T., Regan, S., del Castillo, C. F., and Warshaw, A. L. Diagnosis of pancreatic cystic neoplasms: a report of the cooperative pancreatic cyst study. Gastroenterology, 126: 1330-6, 2004.
4. Lewandrowski, K. B., Southern, J. F., Pins, M. R., Compton, C. C., and Warshaw, A. L. Cyst fluid analysis in the differential diagnosis of pancreatic cysts. A comparison of pseudocysts, serous cystadenomas, mucinous cystic neoplasms, and mucinous cystadenocarcinoma. Ann Surg, 217: 41-7, 1993.
5. Levy, M., Levy, P., Hammel, P., Zins, M., Vilgrain, V., Amouyal, G., Amouyal, P., Molas, G., Flejou, J. F., Voitot, H., and et al. [Diagnosis of cystadenomas and cystadenocarcinomas of the pancreas. Study of 35 cases]. Gastroenterol Clin Biol, 19: 189-96, 1995.
6. Brugge, W. R., Lauwers, G. Y., Sahani, D., Fernandez-del Castillo, C., and Warshaw, A. L. Cystic neoplasms of the pancreas. N Engl J Med, 351: 1218-26, 2004.
7. Hamilton, S. R., and Aaltonen, L. A. WHO Classification of Tumours, Pathology and Genetics of Tumours of Digestive System: Lyon, France: IARC Press, 2000.
8. Kloppel, G., Solcia, E., Longnecker, D., Capella, C., and Sobin, L. Histological typing of tumours of the exocrine pancreas: World Health Organization international histological classification of tumours: Springer-Verlag, 1998.
9. Wilentz, R. E., Albores-Saavedra, J., Zahurak, M., Talamini, M. A., Yeo, C. J., Cameron, J. L., and Hruban, R.

H. Pathologic examination accurately predicts prognosis in mucinous cystic neoplasms of the pancreas. Am J Surg Pathol, 23: 1320-7, 1999.
10. Kloppel, G. Clinicopathologic view of intraductal papillary-mucinous tumor of the pancreas. Hepatogastroenterology, 45: 1981-5, 1998.
11. Sarr, M. G., Carpenter, H. A., Prabhakar, L. P., Orchard, T. F., Hughes, S., van Heerden, J. A., and DiMagno, E. P. Clinical and pathologic correlation of 84 mucinous cystic neoplasms of the pancreas: can one reliably differentiate benign from malignant (or premalignant) neoplasms? Ann Surg, 231: 205-12, 2000.
12. Yeo, T. P., Hruban, R. H., Leach, S. D., Wilentz, R. E., Sohn, T. A., Kern, S. E., Iacobuzio-Donahue, C. A., Maitra, A., Goggins, M., Canto, M. I., Abrams, R. A., Laheru, D., Jaffee, E. M., Hidalgo, M., and Yeo, C. J. Pancreatic cancer. Curr Probl Cancer, 26: 176-275, 2002.
13. Cullen, J. J., Sarr, M. G., and Ilstrup, D. M. Pancreatic anastomotic leak after pancreaticoduodenectomy: incidence, significance, and management. Am J Surg, 168: 295-8, 1994.
14. Jacobson, B. C., Adler, D. G., Davila, R. E., Hirota, W. K., Leighton, J. A., Qureshi, W. A., Rajan, E., Zuckerman, M. J., Fanelli, R. D., Baron, T. H., and Faigel, D. O. ASGE guideline: complications of EUS. Gastrointest Endosc, 61: 8-12, 2005.
15. Li, X. M., Patel, B. B., Blagoi, E. L., Patterson, M. D., Seehozer, S. H., Zhang, T., Damle, S., Gao, Z., Boman, B., and Yeung, A. T. Analyzing alkaline proteins in human colon crypt proteome. J Proteome Res, 3: 821-33, 2004.
16. Ishihama, Y., Oda, Y., Tabata, T., Sato, T., Nagasu, T., Rappsilber, J., and Mann, M. Exponentially modified protein abundance index (emPAI) for estimation of absolute protein amount in proteomics by the number of sequenced peptides per protein. Mol Cell Proteomics, 4: 1265-72, 2005.
17. Eisen, M. B., Spellman, P. T., Brown, P. O., and Botstein, D. Cluster analysis and display of genome-wide expression patterns. Proc Natl Acad Sci USA, 95: 14863-8, 1998.
18. Peterson, L. E. Partitioning large-sample microarray-based gene expression profiles using principal components analysis. Comput Methods Programs Biomed, 70: 107-119, 2003.
19. Schmid, R. M. [Pancreatic cancer]. Schweiz Rundsch Med Prax, 95: 1709-12, 2006.
20. Salama, I., Malone, P. S., Mihaimeed, F., and Jones, J. L. A review of the S100 proteins in cancer. Eur J Surg Oncol, 2007.
21. Ohuchida, K., Mizumoto, K., Ishikawa, N., Fujii, K., Konomi, H., Nagai, E., Yamaguchi, K., Tsuneyoshi, M., and Tanaka, M. The role of S100A6 in pancreatic cancer development and its clinical implication as a diagnostic marker and therapeutic target. Clin Cancer Res, 11: 7785-93, 2005.
22. Ohuchida, K., Mizumoto, K., Ohhashi, S., Yamaguchi, H., Konomi, H., Nagai, E., Yamaguchi, K., Tsuneyoshi, M., and Tanaka, M. S100A11, a putative tumor suppressor gene, is overexpressed in pancreatic carcinogenesis. Clin Cancer Res, 12: 5417-22, 2006.
23. Hammel, P. R., Forgue-Lafitte, M. E., Levy, P., Voitot, H., Vilgrain, V., Flejou, J. F., Molas, G., Gespach, C., Ruszniewski, P., Bernades, P., and Bara, J. Detection of gastric mucins (M1 antigens) in cyst fluid for the diagnosis of cystic lesions of the pancreas. Int J Cancer, 74: 286-90, 1997.
24. Kuespert, K., Pils, S., and Hauck, C. R. CEACAMs: their role in physiology and pathophysiology. Curr Opin Cell Biol, 18: 565-71, 2006.
25. Redefined Nomenclature for Members of the Carcinoembryonic Antigen Family.pdf.
26. Gold, P., and Freedman, S. O. Specific carcinoembryonic antigens of the human digestive system. J Exp Med, 122: 467-81, 1965.
27. Hammel, P., Voitot, H., Vilgrain, V., Levy, P., Ruszniewski, P., and Bernades, P. Diagnostic value of CA 72-4 and carcinoembryonic antigen determination in the fluid of pancreatic cystic lesions. Eur J Gastroenterol Hepatol, 10: 345-8, 1998.
28. Roth, J., Goebeler, M., and Sorg, C. S100A8 and S100A9 in inflammatory diseases. Lancet, 357: 1041, 2001.
29. Ryckman, C., Vandal, K., Rouleau, P., Talbot, M., and Tessier, P. A. Proinflammatory activities of S100: proteins S100A8, S100A9, and S100A8/A9 induce neutrophil chemotaxis and adhesion. J Immunol, 170: 3233-42, 2003.
30. Leach, S. T., Yang, Z., Messina, I., Song, C., Geczy, C. L., Cunningham, A. M., and Day, A. S. Serum and mucosal S100 proteins, calprotectin (S100A8/S100A9) and S100A12, are elevated at diagnosis in children with inflammatory bowel disease. Scand J Gastroenterol: 1-11, 2007.
31. Lu, Z., Hu, L., Evers, S., Chen, J., and Shen, Y. Differential expression profiling of human pancreatic adenocarcinoma and healthy pancreatic tissue. Proteomics, 4: 3975-88, 2004.
32. Zappacosta, F., Collingwood, T. S., Huddleston, M. J., and Annan, R. S. A quantitative results-driven approach to analyzing multisite protein phosphorylation: the phosphate-dependent phosphorylation profile of the transcription factor Pho4. Mol Cell Proteomics, 5: 2019-30, 2006.
33. Keshishian, H., Addona, T., Burgess, M., Kuhn, E., and Carr, S. A. Quantitative, multiplexed assays for low abundance proteins in plasma by targeted mass spectrometry and stable isotope dilution. Mol Cell Proteomics, 2007.
34. Wolf-Yadlin, A., Hautaniemi, S., Lauffenburger, D. A., and White, F. M. Multiple reaction monitoring for robust quantitative proteomic analysis of cellular signaling networks. Proc Natl Acad Sci USA, 104: 5860-5, 2007.
35. Anderson, L., and Hunter, C. L. Quantitative mass spectrometric multiple reaction monitoring assays for major plasma proteins. Mol Cell Proteomics, 5: 573-88, 2006.

While certain of the preferred embodiments of the present invention have been described and specifically exemplified above, it is not intended that the invention be limited to such embodiments. Various modifications may be made thereto without departing from the scope and spirit of the present invention, as set forth in the following claims.

What is claimed is:
1. A method of diagnosing an increased risk for the development of pancreatic cancer in a human test subject, said method comprising:
   a) obtaining a pancreatic cyst fluid specimen from a human test subject;
   b) analyzing said fluid specimen for the presence of at least three biomarkers for pancreatic carcinoma identifiable in said cyst fluid sample via mass spectroscopy, said presence being indicative of an increased risk for pancreatic cancer, said biomarkers being selected from the group consisting of mucin 1, mucin 2, mucin 5AC, mucin 5B, mucin 6, CEA CAM 1, CEACAM 5, CEACAM 6, CEACAM 7, CEACAM 8, S100-A6, S100-A8, S100-A9 and S100-A11, and c) diagnosing said patient as being at increased risk based on the presence of said markers in said sample.

2. The method claim 1, wherein said biomarkers comprise at least three mucins.

3. The method of claim 1, wherein said biomarkers comprise at least two mucins and at least two CEACAMs.

4. The method of claim 2 or 3 further comprising detection of at least one biomarker selected from the group consisting of S100-A6, S100-A8, S100-A9 and S100-A11.

5. The method of claim 1 wherein said diagnosis differentiates a malignant tumor from a benign tumor.

6. The method of claim 1 wherein said diagnosis is an adjunct to a primary diagnostic test for carcinoma of the pancreas.

7. The method of claim 1, wherein three biomarkers are detected, said markers being Mucin 5B, CEACAM 5 and CEACAM 6.

8. A kit for practicing the method of claim 1, comprising reagents suitable for detecting the presence or absence of said at least three biomarkers in said cyst fluid.

9. A kit as claimed in claim 8, comprising a solid support and reagents effective for assessing immune complex formation between said biomarkers and antibodies immunospecific for said biomarkers affixed to said solid support.

* * * * *